(12) United States Patent
Kiel et al.

(10) Patent No.: US 8,628,955 B2
(45) Date of Patent: Jan. 14, 2014

(54) COMPOSITIONS, METHODS AND USES FOR BIOSYNTHETIC PLASMID INTEGRATED CAPTURE ELEMENTS

(76) Inventors: Johnathan L. Kiel, Brooks City-Base, TX (US); Amanda Tijerina, San Antonio, TX (US); Eric A. Holwitt, Brooks City-Base, TX (US); Jill Parker, Brooks City-Base, TX (US); Mark A. Sloan, Spring Branch, TX (US); Melanie Woitaske, La Vernia, TX (US); Maomian Fan, San Antonio, TX (US)

( * ) Notice: Subject to any disclaimer, the term of this patent is extended or adjusted under 35 U.S.C. 154(b) by 254 days.

(21) Appl. No.: 12/792,492

(22) Filed: Jun. 2, 2010

(65) Prior Publication Data
US 2011/0027851 A1 Feb. 3, 2011

Related U.S. Application Data

(60) Provisional application No. 61/183,453, filed on Jun. 2, 2009.

(51) Int. Cl.
*C12N 15/63* (2006.01)
*C07H 21/04* (2006.01)

(52) U.S. Cl.
USPC ...................................... 435/320.1; 536/23.1

(58) Field of Classification Search
None
See application file for complete search history.

(56) References Cited

U.S. PATENT DOCUMENTS 6,303,316 B1 * 10/2001 Kiel et al. .................... 435/6.19

FOREIGN PATENT DOCUMENTS

WO WO2008/029401 3/2008

OTHER PUBLICATIONS

Cox et al. Automated Selection of Anti-Protein Aptamers, Bioorganic & Medicinal Chemistry 9: 2525-2531, 2001.*
Bardhan et al., "Nanoshells with Targeted Simultaneous Enhancement of Magnetic and Optical Imaging and Photothermal Therapeutic Response," Advanced Functional Materials 2009, 19:1-9.
Chakravarthy et al., "Gold nanorod delivery of an ssRNA immune activator inhibits pandemic viral replication," PNAS 2010, 107(22):10172-10177.
Dave et al., "siRNA targeting Vaccinia virus double-stranded RNA binding protein [E3L] exerts potent antiviral effects," Virology 2006, 348:489-497.
de Heer et al., "A Carbon Nanotube Field-Emission Electron Source," Science 1995, 270:1179-1180.
Gierseg et al., "Novel Electroporation System for both Gram-Negative and Gram-Positive Bacteria Assisted by Multi-Walled Carbon Nanotubes," Defense Technical Information Center Compilation Part Notice ADP019734, Materials Research Society Symposium Proceedings 2005, 845:285-290.
Hamad-Schifferli et al., "Direct Electronic Control of Biomolecular Systems: Using Nanocrystals as Antennas for Regulation of Biological Activity," Materials Research Society Symposium Proceedings 2001, 676:Y8.43.1-Y8.43.6.
Hirakawa et al., "Electron emission properties of carbon nanotubes," Applied Surface Science 2001, 669-170:662-665.
Kohli et al., "Smart Nanotubes for Biotechnology," Current Pharmaceutical Biotechnology 2005, 6(1):35-47.
Kubik et al., "Nanotechnology on Duty in Medical Applications," Current Pharmaceutical Biotechnology 2005, 6(1):17-33.
Li et al., "Diamine biomolecules surface functionalization single-walled carbon nanotube as gene-delivery vector," European Cells and Materials 2007, 13(Suppl. 3):24.
Liu et al., "Translocation of Single-Stranded DNA Through Single-Walled Carbon Nanotubes," Science 2009; 327:64-67.
Raffa et al., "Can the properties of carbon nanotubes influence their internalization by living cells?" Carbon 2008, 46:1600-1610.
Richard et al., "Functionalization of Single- and Multi-Walled Carbon Nanotubes with Cationic Amphiphiles for Plasmid DNA Complexation and Transfection," Nano Research 2009, 2:638-647.
Yeh et al., "Nucleic acid transport through carbon nanotube membranes," PNAS 2004, 101(33):12177-12182.
Yehia et al., "Single-walled carbon nanotube interactions with HeLa cells," Journal of Nanobiotechnology 2007, 5:8.
Zhu et al., "Single-walled carbon nanotube as an effective quencher," Analytical and Bioanalytical Chemistry 2010, 396:73-83.

* cited by examiner

*Primary Examiner* — Jennifer McDonald
(74) *Attorney, Agent, or Firm* — Faegre Baker Daniels, LLP

(57) ABSTRACT

Embodiments herein report compositions, systems and methods for making and using plasmid vectors and nanotube complexes. In certain embodiments, compositions, systems and methods herein include making plasmid vectors having aptamer inserts. In some embodiments, methods disclosed herein may be used to rapidly generate large quantities of plasmid vectors having aptamer inserts directed to a particular target agent. Other aspects concern plasmid constructs associated with organic semiconductors. Yet other aspects concern complexes of nanotubes associated with dsDNA aptamers and tracking molecules.

15 Claims, 19 Drawing Sheets

A.
B.
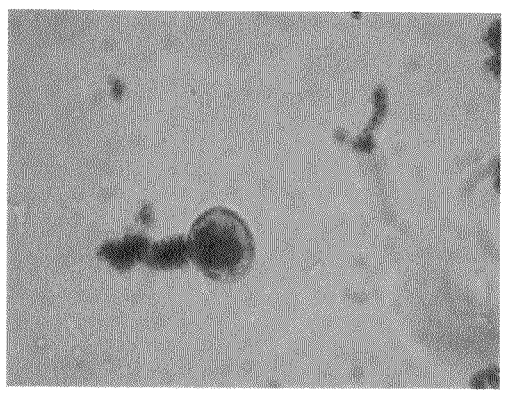
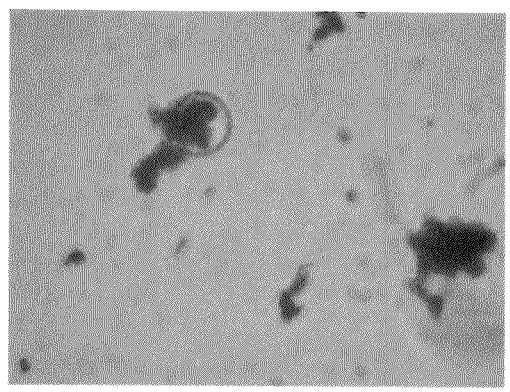
C.
D.
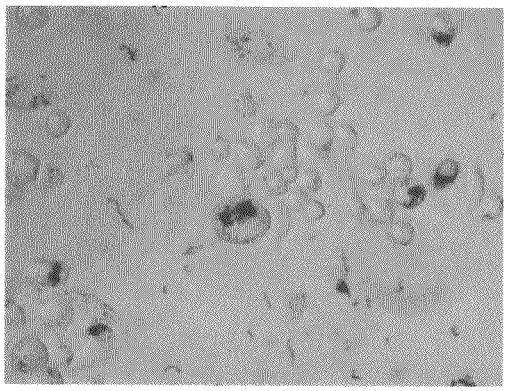
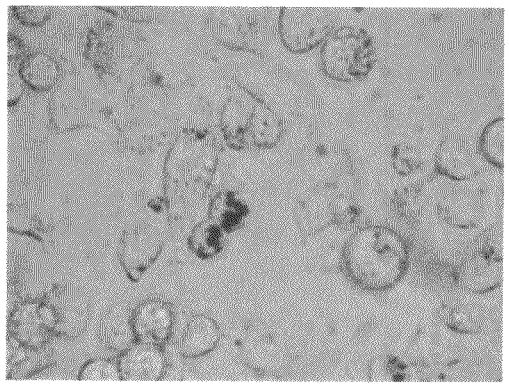
FIG. 8A-D

A.
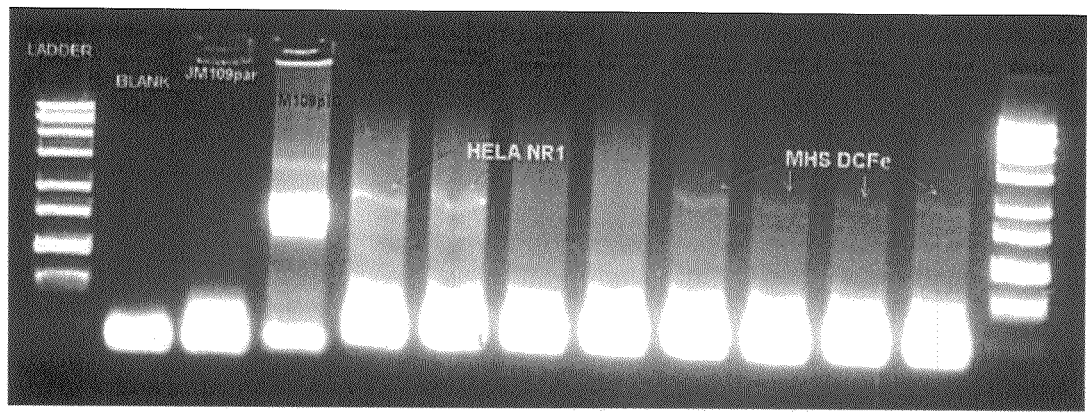
B.
FIG. 9A-B

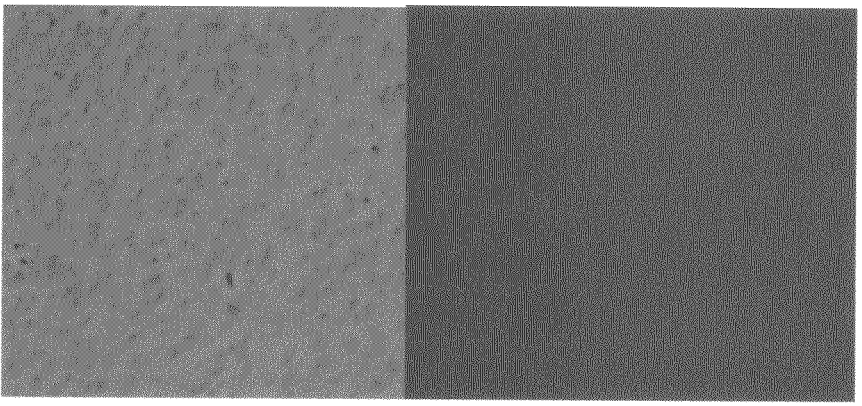
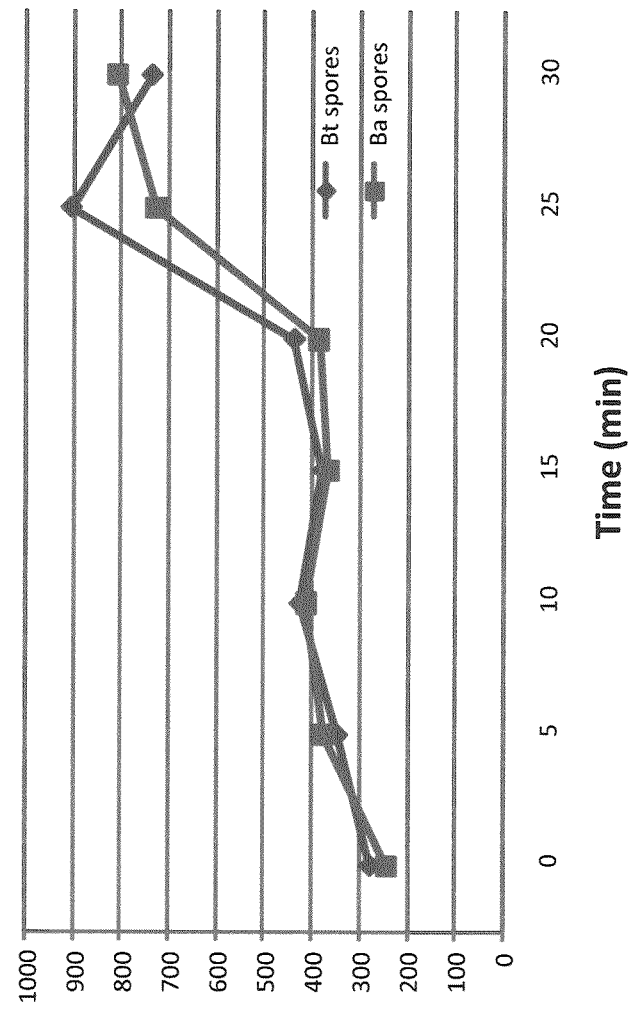
FIG. 12

Arrows show intracellular aggregate nanobe structures

COMPOSITIONS, METHODS AND USES FOR BIOSYNTHETIC PLASMID INTEGRATED CAPTURE ELEMENTS

CROSS REFERENCE TO RELATED APPLICATIONS

The present application claims the benefit under 35 U.S.C. 119(e) of U.S. Provisional Patent Application Ser. No. 61/183,453 filed on Jun. 2, 2009 which is incorporated herein by reference in its entirety.

STATEMENT REGARDING FEDERALLY FUNDED RESEARCH

The U.S. Government has a paid-up license in this invention and the right in limited circumstances to require the patent owner to license others on reasonable terms as provided for by the terms of Contract No. F41624-D-7000 awarded by the United States Air Force.

FIELD

Embodiments herein relate to compositions, systems, and methods for making and using plasmid vectors. In certain embodiments, compositions, systems and methods herein include making plasmid vectors having aptamer inserts. In some embodiments, methods disclosed herein may be used to rapidly generate large quantities of plasmid vectors directed to a particular target agent. In other embodiments, compositions, systems, uses and methods relate to generating nanotube complexes. Methods, systems and compositions disclosed herein may be used for detection, drug development, drug delivery, identification, collection, decontamination, analysis of disease detection or progression, neutralization, determination of viability, and/or inactivation or killing of a target agent.

BACKGROUND

Aptamers are single-stranded nucleic acids isolated from random-sequence nucleic acid libraries by selection such as in vitro selection. Many DNA or RNA sequences have been isolated that bind a diverse range of targets, including metal ions, small organic compounds, biological cofactors, metabolites, proteins and nucleic acids. The target versatility and the high binding affinity of both DNA and RNA aptamers, their properties of precise molecular recognition, along with the simplicity of in vitro selection, make aptamers attractive as molecular receptors and sensing elements.

Current methods, techniques and devices used for identifying chemical and biological analytes typically involve capturing the analyte through use of a non-specific solid surface or through capture deoxyribonucleic acids (DNA) or antibodies. A number of known binding agents must then be applied, particularly in the case of biological analytes, until a binding agent with a high degree of affinity for the analyte is identified such as an aptamer. A labeled aptamer (e.g., labeled DNA) must be applied, where the aptamer causes, for example, the color or fluorescence of the analyte to change if the binding agent exhibits affinity for the analyte (i.e., the binding agent binds with the analyte). The aptamer may be identified by studying which of the various binding agents exhibited the greatest degree of affinity for the analytes.

Some problems associated with current methods of chemical and biological agent identification include that a great deal of time and effort is required to repetitiously generate and apply each of the known labeled aptamers, until an aptamer exhibiting a high degree of affinity is found. In addition, once the identification of a high affinity aptamer is made the synthesis of multiple copies for use becomes a challenge. Accordingly, these techniques are not conducive to easy automation. Current methods are also not sufficiently robust to work in environmental conditions, for example, heat, dust, humidity or other conditions that may be encountered, for example, in the field or in a food processing plant. Portability and ease of use are also problems seen with current methods for chemical and biological agent identification.

SUMMARY

Embodiments herein report compositions, systems and methods for making and using plasmid vectors. In certain embodiments, compositions, systems and methods herein include making plasmid vectors having aptamer inserts. In some embodiments, methods disclosed herein may be used to rapidly generate large quantities of plasmid vectors directed to a particular target agent. Methods, systems and compositions disclosed herein may be used for detection, drug development, drug delivery, identification, collection, decontamination, analysis of disease detection or progression, neutralization, determination of viability, and/or inactivation or killing of a target agent.

Some embodiments of the present invention report using nanotubes as quenching agents in constructs described herein. In accordance with these embodiments, a nanotube construct may be used in cellular transfection to deliver a targeting molecule (e.g. targeting an agent in a eukaryotic cell for destruction, detection or modification etc.). In certain embodiments, a nanotube construct may be referred to as a nanobe wherein the nanobe includes, but is not limited to, a nanoparticle associated with a single-stranded DNA (ssDNA) consensus sequence capable of hybridizing to a complementary sequence, the ssDNA associated with a nanotube. In some embodiments, the nanobe complex can penetrate a cell (e.g. a eukaryotic cell). In some examples, cells may be transfected in order to modify cells that then modify an organism (e.g. generate non-virulent forms, non-pathogenic forms or the like, generate organisms sensitive to certain types of destruction or to design self-destructing strains or cells etc.). In other embodiments, cells may be transfected in order to deliver an agent to the cell (e.g. a drug, a detection agent, targeting agent etc.).

In other embodiments, a plasmid complex composition may include one or more plasmids with at least one selectable marker, having one or more random aptamers inserted into the plasmid, and an organic semiconductor associated with the one or more plasmids, wherein the aptamer inserted plasmids and the organic semiconductor forms a plasmid-random aptamer-organic semiconductor complex. In certain compositions, a plasmid-random aptamer-organic semiconductor complex can further include nanoparticles or microbeads, wherein the nanoparticles or microbeads non-covalently associate with the plasmid-random aptamer-organic semiconductor complex. In other embodiments, plasmid-random aptamer-organic semiconductor complexes that bind to a target agent through recognition by random aptamers may be selected before or after association with nanoparticles or microbeads. Selected plasmid complexes that bind to the target agent may be cloned by introduction to a bacterial or mammalian culture or amplified. In addition, selected plasmid-random aptamer complexes may further be linked to an organic semiconductor if grown in a bacterial culture capable of producing organic semiconductors. Alternatively, selected plasmid-random aptamer complexes may be linked to an organic semiconductor by synthetic addition of an organic semiconductor to the selected plasmid-random aptamer complexes.

In other embodiments, a plasmid complex composition may include one or more plasmids or dsDNA with at least one selectable marker, having one or more random aptamers inserted into the plasmid or linked to the dsDNA and a nanotube (e.g. single-walled carbon nanotube) associated with the one or more plasmids or dsDNA and one or more fluor, wherein the aptamer(s) insert and the nanobe forms a plasmid/dsDNA-random aptamer-fluor-nanobe complex. In certain compositions, a plasmid/dsDNA-random aptamer-fluor-nanobe complex can further include nanoparticles or microbeads, wherein the nanoparticles or microbeads non-covalently associate with the plasmid/dsDNA-random aptamer-fluor-nanobe complex (or random aptamer-fluor-nanobe complex). In other embodiments, plasmid/dsDNA-random aptamer-fluor-nanobe complexes that bind to a target agent through recognition by random aptamers may be selected before or after association with nanoparticles or microbeads. Selected plasmid complexes that bind to the target agent may be cloned by introduction to a bacterial or mammalian culture. In addition, selected plasmid-random aptamer complexes may further be linked to a nanobe if grown in a bacterial culture capable of producing nanobes. Alternatively, selected plasmid-random aptamer complexes may be linked to a nanobe by synthetic addition of an organic semiconductor to the selected plasmid-random aptamer complexes.

It is contemplated herein that some constructs (e.g. nanobe constructs) may be used as a sensor for condition of a cell or cell component, for example, by detecting the presence or absence of fluorescence of a construct disclosed herein due to target agent concentrations, levels, or existence.

Other embodiments of the present invention may concern using nanoparticles or microbeads associated with plasmid complexes disclosed herein to immobilize plasmid complexes or select out plasmid complexes that specifically bind to a target agent. In certain embodiments, the nanoparticles or microbeads associate with the selected plasmid complexes covalently or non-covalently. Nanoparticles or microbeads can be paramagnetic nanoparticles, quantum dots, nanostructures, colloidal gold, colloidal silver, iron nanoparticles, platinum nanoparticles, microspheres, or nanospheres.

In some aspects, target agents may include, but are not limited to, whole organisms, inorganic, organic or biochemical targets such as a virus, bacteria, yeast, spore, metal ions, small organic compounds, biological cofactors, metabolites, proteins, nucleic acids, biological warfare agents, terrorism agents, natural or genetically modified agents. In other embodiments, a target agent may be a protein, peptide, antibody, antibody fragment, polysaccharide, lipid, or nucleic acid.

Samples contemplated herein can be, but are not limited to, samples from a subject such as human samples, mammalian samples, bird samples or reptile samples (e.g. blood, buccal, nasal, tissue, urine, skin). In some embodiments, a sample can be obtained from a domesticated animal for example, a dog, cat, bird or farm animal.

In addition, samples reported herein can include one or more samplings from an inanimate object including, but not limited to, air filters, a solid surface, mail, an outer surface of an object, a filter, a vent, a duct, an aerosol collected on a filter, an unknown powder, dusty agent sample, any surface of an object, such as a counter, wall, a table, a chair, equipment (e.g. military equipment); or any other surface that a subject may come in contact with; or a sample from food, soil, or water source.

In some embodiments, the plasmid complex may be further immobilized on a solid substrate. Solid substrates contemplated herein include, but are not limited to, microbeads, magnetic beads, a microarray, a microtiter plate or other solid surface known in the art.

Other aspects of the present invention include methods for producing a plasmid complex directed to bind one or more target agents. In accordance with these aspects, methods can include inserting random nucleic acid aptamers into plasmids having selectable markers then, making random aptamer-plasmid constructs in a host organism; obtaining one or more target agents associated with nanoparticles to make target agent-nanoparticle complexes; introducing target agent-nanoparticle complexes to the host organism having the random aptamer-plasmid constructs or to extracted random aptamer-plasmid constructs; and isolating the random aptamer-plasmid constructs associated with the target agent-nanoparticle complexes. In addition, other embodiments for producing plasmid complexes directed to bind a target agent may include, but are not limited to, introducing the isolated random aptamer-plasmid constructs associated with the target agent-nanoparticle to a random aptamer-plasmid construct-free bacterial culture to make random aptamer-plasmid construct producing clones; selecting the clones having the selectable marker, wherein the clones having the selectable marker have random aptamer-plasmid constructs associated with the target agent-nanoparticle complexes and wherein the random aptamer-plasmid specifically recognizes the target agent.

Alternatively, selected clones may be grown on media, wherein the media permits synthesis of organic semiconductors by the clone and wherein the organic semiconductor associates with the selected random aptamer-plasmid constructs making a organic semiconductor-selected random aptamer-plasmid complex capable of targeting the target agent. Organic semiconductor-selected random aptamer-plasmid complex may be further immobilized on a surface.

Other embodiments can include methods for using a plasmid complex disclosed herein. For example, methods are disclosed for using an organic semiconductor-selected aptamer-plasmid complex. Other embodiments include methods for using a plasmid/dsDNA random aptamer-fluor—nanotube complex. Nanotubes and target DNA (e.g aptamers) can combine to form a stable biosensor or biodetector complex. Methods may include, but are not limited to, obtaining a complex; exposing a sample suspected of having a target agent to the complex; and allowing the complex to bind to the target agent if present in the sample. Some samples may include, but are not limited to, inanimate, non-living samples for example, samples from a solid surface, mail, an outer surface of an object, a filter, a vent, a duct, field samples, military gear, military equipment, soil or other inanimate object suspected of having a target agent. In certain embodiments of the present invention, a complex may be used to detect, identify or destroy a target agent(s). In accordance with these embodiments, methods may further include, exposing the complex bound to a target agent to an energy source capable of destroying, killing or neutralizing the target agent.

Energy sources contemplated herein may include, but are not limited to, microwave radiation, ultraviolet radiation (UV), visible light, laser, electron beam radiation, pulsed corona discharge (non-thermal plasma discharge), other forms of ionizing radiation, and thermal radiation. Other embodiments may include, introducing an attractant (e.g. magnetic beads, column chromatography with streptavidin-biotin or other molecule) to the complex bound to the target agent and concentrating the complex bound to the target agent for further analysis using the attractant to concentrate the target agent. Energy sources contemplated of use herein may be used for detection, modification or destruction of an organism or cell or other target agent.

Certain embodiments may include immobilizing a complex contemplated herein on a surface for example, a solid surface. Solid surfaces for immobilizing a complex contemplated may include, but are not limited to, glass, plastic, silicon-coated substrate, macromolecule-coated substrate, particles, beads, microparticles, microbeads, dipstick, magnetic beads, paramagnetic beads and a combination thereof.

Other aspects contemplated herein may include a system for detecting a complex disclosed herein. Certain embodiments for a system may include an element for inputting random aptamers in a reaction vessel; and a component for inputting the random aptamers into a plasmid having at least one selectable marker of a first bacterial or first mammalian organism to make random aptamer-plasmid complexes; an element for isolating the random aptamer-plasmid complexes and introducing the random aptamer-plasmid complexes to a second bacterial organism capable of making organic semiconductors in another reaction vessel wherein the organic semiconductor associates with the random aptamer-plasmid complexes; and isolating the organic semiconductor-selected random aptamer-plasmid complex. Other embodiments may include, a system having component for selecting organic semiconductor-selected aptamer-plasmid complexes that bind to a target agent.

Other embodiments may include a kit for making and/or using complexes including, but not limited to, a source of plasmids; a source of nanoparticles; and a source for generating organic semiconductors or other quenching agent complexes such as nanobes. A kit may further include magnetic beads or other material capable of attracting and/or concentration nanoparticles.

Example kits may include, but are not limited to, one or more complexes capable of binding one or more target molecule able to detect, identify, decontaminate, analyze disease progression, neutralize, determine viability, inactivate, kill or combination thereof. In some embodiments, a kit may be generated for both detecting and destroying, detecting and decontaminating, detecting and identifying, detecting and neutralizing, detecting and obliterating, detecting and further analyzing one or more target agents. Certain kits are directed to particular target molecules and the target molecules can include, but are not limited to, whole organisms. In some embodiments, a kit can be used to generate plasmids having aptamers specific for binding a target molecule or a kit may already have a lyophilized composition of plasmids having selected aptamers capable of recognizing a target agent. Some kits may contain a partially or completely dehydrated composition including, but not limited to, a bacterial host having a plasmid harboring a random aptamer library or pre-selected aptamer, the host bacterial having the capability of producing organic semiconductors. Alternatively, a kit may include a partially or completely dehydrated composition of a plasmid harboring a random aptamer library or pre-selected aptamer capable of being introduced to a bacteria culture for expansion.

In certain embodiments, a kit can contain partially or completely dehydrated complexes reported herein and these complexes can be re-hydrated and expanded and used to assess the presence and/or level of a target agent(s). In accordance with these embodiments, a target agent may be in a sample from a subject suspected of having or at risk for developing a disorder where the target agent is indicative of the onset, progression or existence of the disorder. In addition, a target agent may be present in a remote region where detection and destruction of the agent may be required. In accordance with these embodiments, complexes may be used to select one or more aptamers capable of binding a target agent, amplifying the selected complex and using the amplified selected complexes to bind to the target agent and destroy the agent by introducing a source of energy of the present invention.

In some aspects of the invention, beads or particles contemplated herein can include, but not limited to, paramagnetic beads, magnetic beads, superparamagnetic beads, streptavidin coated beads, Reverse Phase magnetic beads, carboxy terminated beads, hydrazine terminated beads, Silica (sodium silica) beads and IDA (iminodiacetic acid) modified beads, aldehyde modified beads, Epoxy activated beads, DADPA-modified beads (beads with primary amine surface group), biodegradable polymeric beads, amino-polystyrene particles, carboxyl-polystyrene particles, Epoxy-polystyrene particles; dimethylamino-polystyrene particles, hydroxy-polystyrene particles, colored particles, flow cytometry particles, and sulfonate-polystyrene particles. In accordance with these embodiments, a target agent may be covalently or non-covalently linked to a bead or particle. Alternatively, complexes may be immobilized using any bead or particle reported herein.

In certain embodiments, the nucleic acid sequences or aptamers may be sequences of 1 to 1000, 10 to 500, 10 to 250, 10 to 150, 10 to 75, 20 to 60, 15 to 45, 20 to 40 nucleotides or base pairs in length, a single length, a combination of lengths or mixture thereof or combination thereof.

In another embodiment, amplification of selected aptamers (e.g. from a plasmid complex) that bind a target agent can be used to generate multiple copies of the aptamers (e.g. DNA), hybrid molecules or RNA aptamers that bind a target agent. Methods useful for amplifying the partitioned sequences may include, but are not limited to, polymerase chain reaction (PCR), the ligase chain reaction (LCR) Q beta Replicase, an isothermal amplification method, Strand Displacement Amplification (SDA), Repair Chain Reaction (RCR), transcription-based amplification systems (TAS), including nucleic acid sequence based amplification (NASBA) and 3SR.

BRIEF DESCRIPTION OF THE DRAWINGS

The following drawings form part of the present specification and are included to further demonstrate certain embodiments. The embodiments may be better understood by reference to one or more of these drawings in combination with the detailed description of specific embodiments presented herein.

FIG. 8A-8D represent exemplary photographs of views through an inverted microscope of uptake of various nanoparticles by exemplary cells.

FIGS. 9A-9B represent exemplary electrophoresis gels of (A) positive control cell cultures having an exemplary plasmid complex and cells exposed to a nanoparticle composition and (B) a different exposure of (A), human HeLa cells and mouse MHS cells.

FIG. 12 represents fluorescent change after bacterial spores introduced into a quenching system.

DESCRIPTION OF ILLUSTRATIVE EMBODIMENTS

Definitions

Figure 1:
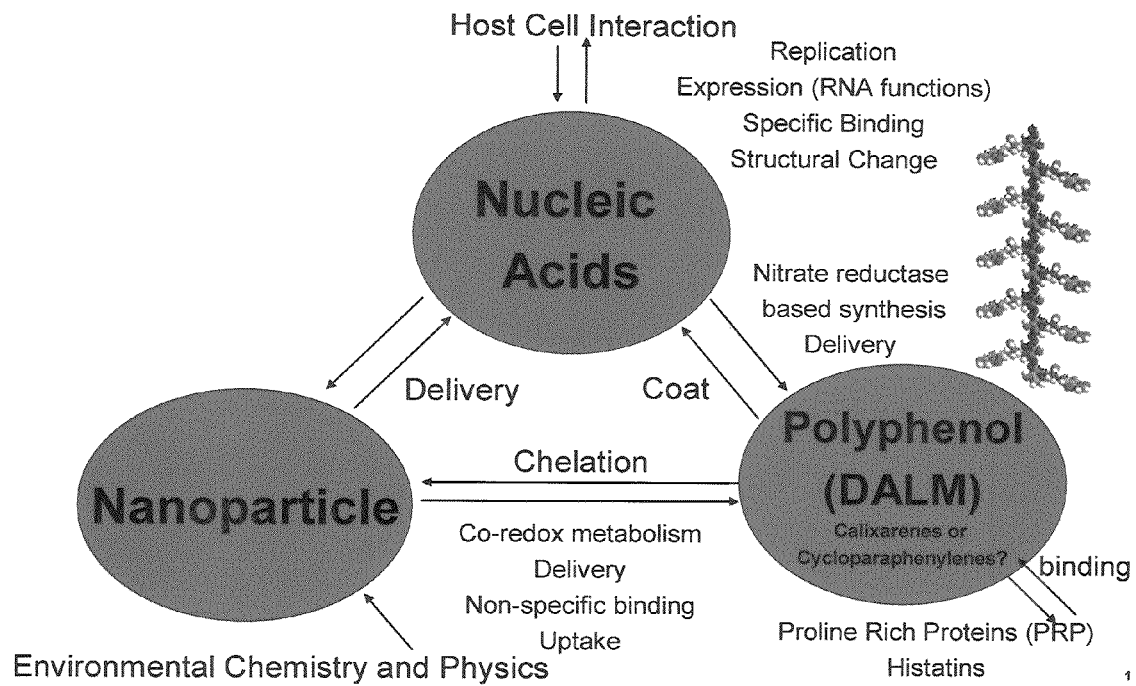
FIG. 1 represents an exemplary schematic of nucleic acid nanoparticle and organic semiconductor interactions.
Figure 2:
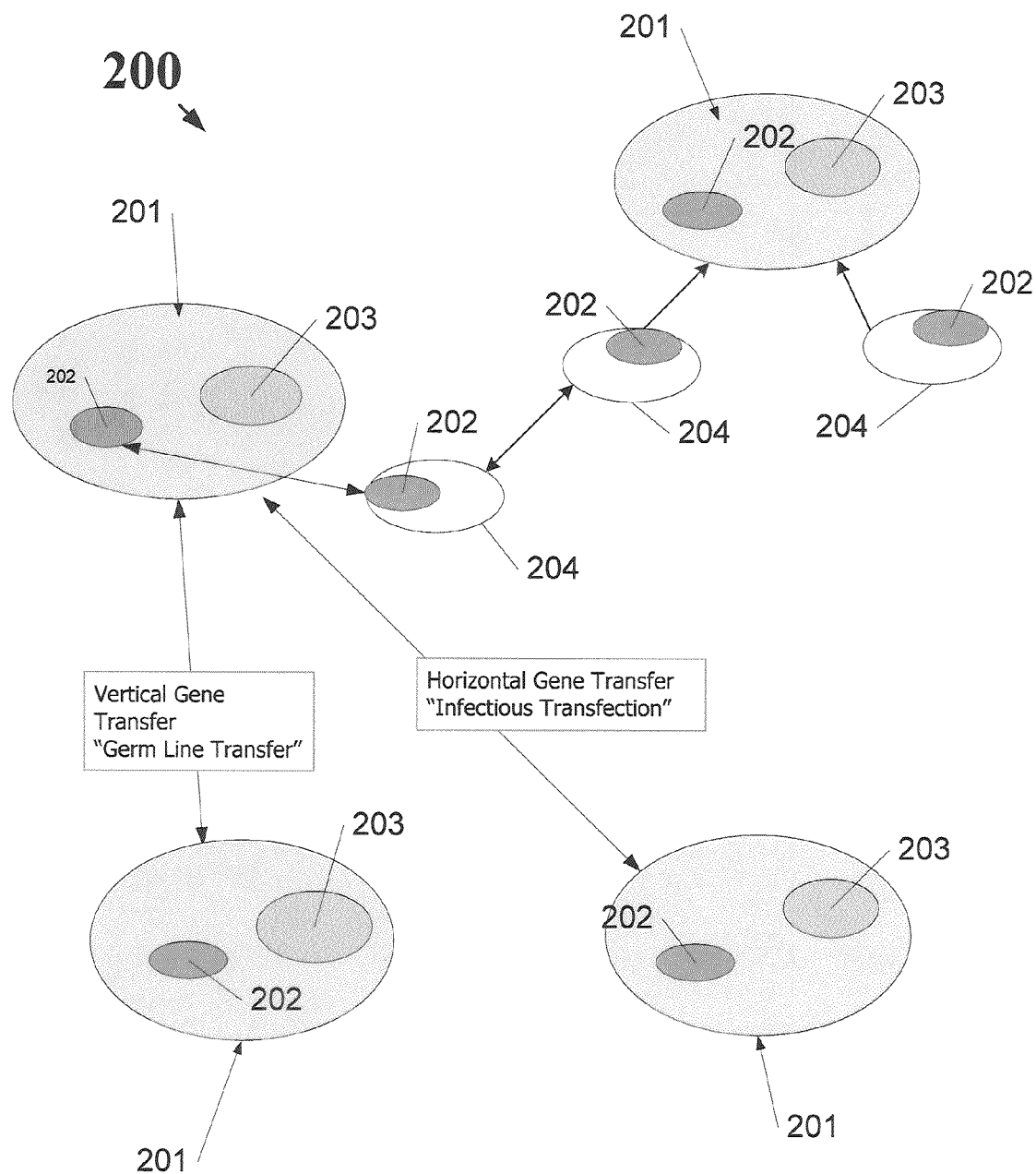
FIG. 2 represents an exemplary schematic of germ line transfer and gene transfer in a cell.
Figure 3:
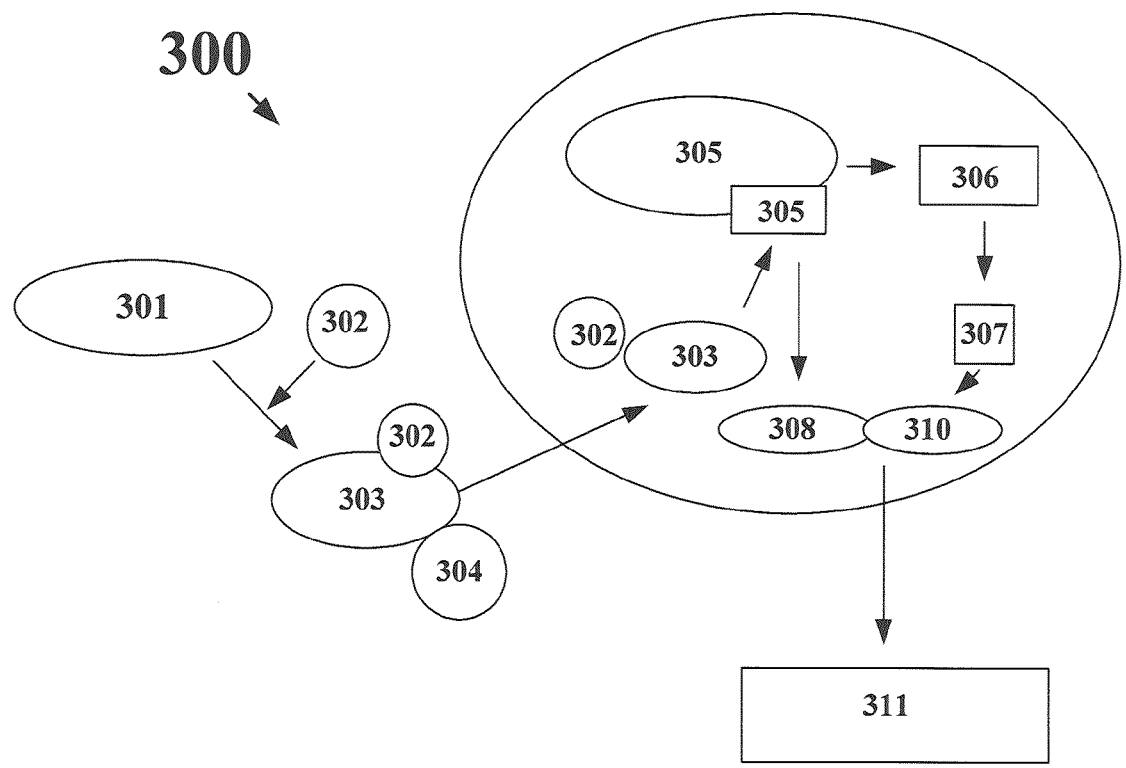
FIG. 3 represent an exemplary schematic of organic semiconductor-selected aptamer-plasmid complex from a random aptamer library.
Figure 4:
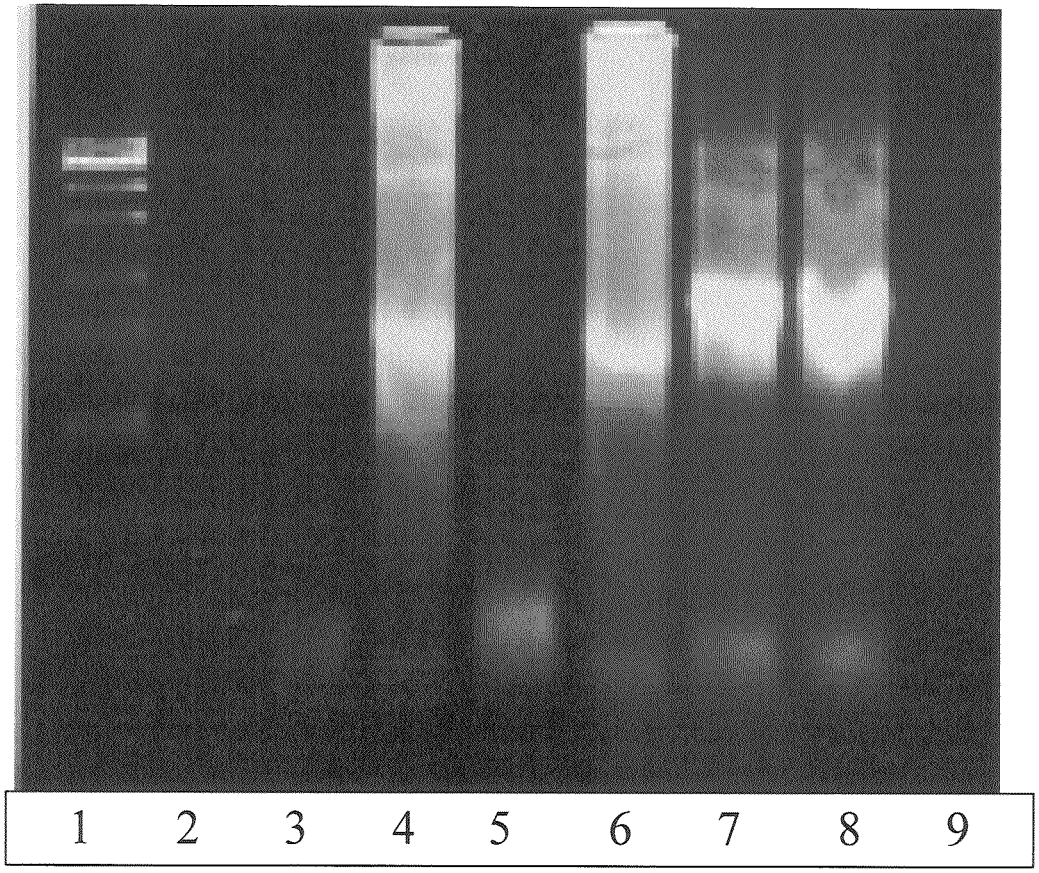
FIG. 4 represents an exemplary electrophoresis gel used for isolating nucleic acids after exposure to a plasmid complex.
Figure 5:
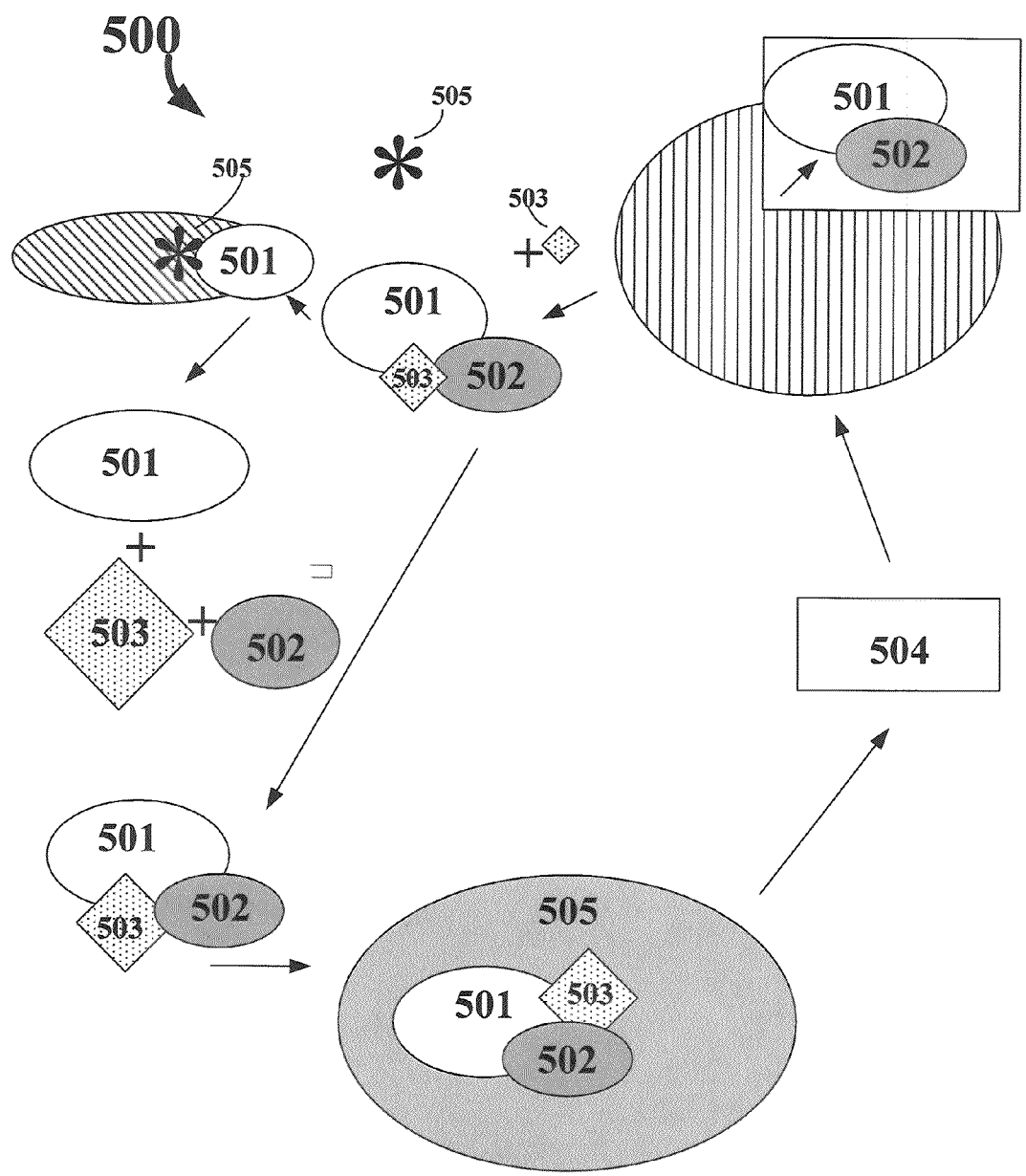
FIG. 5 represents an exemplary schematic of aptamer selection and replication/expansion of predetermined target agent binding aptamers.

As used herein, "a" or "an" may mean one or more than one of an item.

"Nucleic acid" can mean DNA, RNA, single-stranded, double-stranded, hybrid molecules such as RNA/DNA or triple stranded and any chemical modifications thereof. Virtually any modification of the nucleic acid is contemplated herein. "Nucleic acid" encompasses, but is not limited to, oligonucleotides and polynucleotides. "Oligonucleotide" refers to at least one molecule of between about 3 and about 100 nucleotides in length. "Polynucleotide" refers to at least one molecule of greater than about 100 nucleotides in length. These terms generally refer to at least one single-stranded molecule, but in certain embodiments also encompass at least one additional strand that is partially, substantially or fully complementary in sequence. Thus, a nucleic acid may encompass at least one double-stranded molecule or at least one triple-stranded molecule that comprises one or more complementary strand(s) or "complement(s)." As used herein, a single stranded nucleic acid may be denoted by the prefix "ss", a double stranded nucleic acid by the prefix "ds", and a triple stranded nucleic acid by the prefix "ts."

Within the practice disclosed herein, a "nucleic acid" may be of almost any length, from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10000, 15000, 20000 or even more bases in length. In some embodiments, nucleic acid sequences may be around 10 to around 200 bases in length. In other embodiments, double-stranded DNA molecules (dsDNA) may be around 2 to 1000, 10 to 500, 10 to 250, 10 to 150, 10 to 75, 20 to 60, or 15-45 base pairs in length.

The term "nucleic acid" as used herein can generally refer to at least one molecule or strand of DNA, RNA or a derivative or mimic thereof, comprising at least one nucleobase. A "nucleobase" refers to a heterocyclic base, for example, a purine or pyrimidine base naturally found in DNA (e.g. adenine "A," guanine "G," thymine "T" and cytosine "C") or RNA (e.g. A, G, uracil "U" and C), as well as their derivatives and mimics. A "derivative" refers to a chemically modified or altered form of a naturally occurring molecule, while "mimic" and "analog" refer to a molecule that may or may not structurally resemble a naturally occurring molecule, but that function similarly to the naturally occurring molecule. One function of a nucleobase is to hydrogen bond to other nucleobases. Nucleobases can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

A nucleic acid may include, or be composed entirely of, at least one nucleobase, a nucleobase linker moiety and/or a backbone moiety.

As used herein, a "moiety" generally can refer to a smaller chemical or molecular component of a larger chemical or molecular structure, and is encompassed by the term "molecule." In some embodiments, a moiety can be a component of a larger molecule, for example, a reporter agent moiety or a signal reducing agent moiety.

"Aptamer," "DNA capture element" (DCE), "RNA capture element," or hybrid capture element as used herein can mean non-naturally occurring nucleic acid molecules (such as nucleic acid sequences) having a desirable action on a target agent (e.g. binds to a target agent). In some embodiments, actions on a target agent can include, but is not limited to, binding, reacting with covalently attaching target agent; facilitating reaction(s) between the target agent and another molecule (e.g destruction by an organic semiconductor exposed to an energy source), killing and/or neutralizing the target agent. Capture elements or aptamers herein can include, but are not limited to, nucleic acids that are generated and/or identified by methods and compositions disclosed herein. Binding interactions of DCEs or aptamers may not encompass standard nucleic acid/nucleic acid hydrogen bond formation exemplified by Watson-Crick basepair formation (e.g., A binds to U or T and G binds to C), but may encompasses all other types of non-covalent (or in some cases covalent) binding. Non-limiting examples of non-covalent binding include hydrogen bond formation, electrostatic interaction, Van der Waals interaction and hydrophobic interaction. A DCE or any other aptamer contemplated herein may bind to another molecule by any or all of these types of interaction, or in some cases by covalent interaction. Covalent binding of a DCE to another molecule may occur where the DCE or target molecule contains a chemically reactive or photoreactive moiety. The term DCE can include a DNA capture element that is capable of forming a complex with an intended target agent. "Target-specific" means that the DCE binds to a target agent with a much higher degree of affinity than it binds to other materials.

"Analyte," "target," "target agent" and "target analyte" as used herein can mean any compound, whole organism, object, or aggregate of interest. Target agents can include, but are not limited to, a whole organism (e.g. bacteria, yeast or virus), protein, peptide, carbohydrate, polysaccharide, glycoprotein, lipid, hormone, receptor, antigen, allergen, antibody, substrate, metabolite, cofactor, enzyme, metal ion, inhibitor, drug, pharmaceutical, nutrient, toxin, poison, explosive, pesticide, chemical warfare agent, biohazardous agent, prion, radioisotope, vitamin, heterocyclic aromatic compound, carcinogen, mutagen, narcotic, amphetamine, barbiturate, hallucinogen, waste product, contaminant or other molecule. Molecules of any size can serve as target agents. "Target agents" are not limited to single molecules, but may also comprise complex aggregates of molecules, such as a virus, bacterium, spore, mold, yeast, algae, amoebae, dinoflagellate, unicellular organism, pathogen or cell. In certain embodiments, a sample suspected of having a particular bacterium present, such a pathogenic bacteria, may be a target agent of some embodiments of the present invention. Virtually any chemical or biological effector would be a suitable target.

"Binding" as used herein can mean an interaction, association or binding between a target agent and an aptamer, resulting in a sufficiently stable complex so as to permit separation of aptamer:target complexes from uncomplexed aptamers under given binding or reaction conditions. Binding is mediated through hydrogen bonding or other molecular forces.

"Magnetic bead," "paramagnetic bead," "nanoparticle," "magnetic particle" and "magnetically responsive particle" as used herein can mean any particle dispersible or suspendable in aqueous media, without significant gravitational settling and separable from suspension by application of a magnetic field.

"Bound," as used herein can mean covalently or non-covalently associated with a molecule.

"Nanobe," as used herein can mean a nanotube complex or a complete complex of a single or double-walled carbon nanotube, with a paramagnetic or other metallic nanoparticle for directing by magnetic field and enhancing delivery, by electric field focusing, of functional DNA, RNA or modified nucleic acids into target cells, and with polymeric coating to facilitate such delivery. Nanobes are infectious, viral-like synthetic particles that not only can alter function of the cell but can also propagate the nucleic acid by incorporation into cellular DNA and by expressing proteins that can synthesize more DNA or RNA and polymeric coating to deliver that DNA or RNA to other uninfected cells.

"Nanotube" as used herein can mean a carbon nanotube molecule of pure carbon that are long and thin and shaped like tubes, about 1-3 nanometers in diameter, and hundreds of nanometers to micrometers long.

In the following sections, several embodiments of, for example, compositions and methods are described in order to thoroughly detail various embodiments herein. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description to prevent unnecessary masking of various embodiments.

In some embodiments, *bacillus* spores, botox spores, anthrax spores, Shiga toxin (protein), Botox toxins (different types), Ms-2 bacterial, Ovalbumin, (protein) *Yersinia pestis* (vaccine), *Rickettsia* (antigen), VEE (Venezuelan Equine Encephalitis), Vaccinia viruses or a combination of organisms and organism byproducts are contemplated as target agents for aptamers contemplated.

In other embodiments, an aptamer can be selected to bind small organic molecules that include, but are not limited to, small, organic ligands, amino acids, nucleotides and derivatives, biological cofactors, antibiotics or other small molecules from random aptamer intergrated plasmids. In accordance with these embodiments, small molecules can include, but are not limited to, one or more of the following, organic dyes, Theophyllin, 1EHT, Dopamine, Hoechst 33258, sulforhodamine B, Sulforhodamine B, Cellobiose, D-tryptophan, L-arginine, L-citrullin, L-argininamide, L-arginine, L-arginine Mirror-image, L-valine, L-isoleucine, AMP, AMP Mirror-image, Guanosine, FMN, NAD, Vitamin B12, 8-oxo-dG, 5'-cap, Xanthene, Kanamycin A, Lividomycin, Tobramycin, Neomycin B, Viomycin, Chloramphenicol, Streptomycin, Rev peptide, Vasopressin Mirror-image and a combination thereof.

In certain aspects, compositions, methods and systems disclosed herein could be employed in the identification of and/or destruction of target agents; diagnosis and treatment of disease in a sample; to develop new compounds for pharmaceutical use, medical or industrial purposes; or to identify chemical and biological warfare target agents on a military facility, in an area suspected of harboring target agents or out in the field.

Aptamers contemplated herein may be generated by any means known in the art and used as tools in a variety of ways. Random aptamers, partially selected pools of aptamers or selected aptamers that bind to a target agent can be inserted into a plasmid construct. Random libraries may contain a variety of lengths of aptamer sequences and insertions into plasmid can be of the same or different lengths depending on conditions for insertion and sizes of inserts. For example, methods and compositions described in U.S. application Ser. No. 11/965,039 filed Dec. 27, 2007 entitled “Methods and Compositions for Processes of Rapid Selection and Production of Nucleic Acid Aptamers,” incorporated herein by reference in its entirety, or using Selex or other methods known in the art may be used to generate a random library of aptamers or other a specific aptamer for insertion into a plasmid.

Other aspects concern immobilizing a target molecule on a suitable surface, such as microbeads or an array, such as a microarray format. One advantage for using a microarray format is the ability to examine thousands of molecules in a sample, simultaneously. In accordance with these aspects, a target molecule may be immobilized and a plasmid having an aptamer library may be used to select specific binding molecules against the target molecule. Some methods used to immobilize a target molecule are based on covalent, affinity or electrostatic interactions between a target molecule and a suitable surface. Aptamers that bind to an immobilized target molecule can be rapidly identified, isolated and amplified for use in methods and systems disclosed herein.

Uses

In some embodiments, aptamers may be generated for use against any target agent contemplated herein. It is contemplated that aptamers or aptamer-plasmid complexes or aptamer-fluor-nanotube complexes may be produced for diagnostic arrays, portable and/or handheld diagnostic/detection devices, cellular transfection methods, portable kits, or as agents to control, revert, or eliminate the target agent.

Some advantages herein include advantages over some current technologies. One advantage of compositions, methods and systems disclosed herein include rare binding sequences (e.g. for generating low frequency aptamers) in the early stages of selection are preserved (versus eliminated by other technologies) and can be amplified as a selected clone to a predetermined target agent. In addition, methods and systems disclosed herein can allow for the selection and amplification of all binding sequences from the very first round of selection of a specific clone. This can eliminate the need for subsequent rounds of selection while providing a source of one or more specific aptamers permitting a more stable supply of a select aptamer as a clone. Once an aptamer clone, for example, can be identified, isolated, and optionally amplified, and sequenced, these aptamer clones may be subjected to a more rigorous selection process under more stringent conditions of binding. In accordance with these embodiments, aptamer clones with a higher affinity, avidity and greatest specificity can be separately or simultaneously selected. In certain embodiments, a plasmid-aptamer complex identified as a clone may be stored or amplified after storage (e.g. aliquoted and frozen). In certain aspects, a plasmid-aptamer complex may be associated with an organic semiconductor or other agent (e.g. nanobe) and the complex stored in a host organism for later use (e.g. aliquoted, frozen or freeze dried).

In other embodiments, using a modified existing flow cytometer, particle counter or sorter, one could use a hand held magnetic aptamer or plasmid aptamer complex reader in order to capture an aptamer or plasmid-aptamer complex associated with target agents. A captured magnetic complex may be removed from a capture cassette of the reader and amplified, for example, by clonal expansion.

In certain embodiments contemplated herein, luminescent colloidal semiconductor nanocrystals (e.g. quantum dots, qdot) that are inorganic fluorophores can be used in methods disclosed herein to circumvent some of the functional limitations encountered by organic dyes. In other embodiments, organic dyes known in the art may be used, if appropriate. Quantum dots are semiconductors whose conducting characteristics are closely related to the size and shape of the individual crystal. In general, the smaller the size of the crystal, the larger the band gap, the greater the difference in energy between the highest valence band and the lowest conduction band becomes, therefore more energy is needed to excite the dot, and concurrently, more energy is released when the crystal returns to its resting state. One advantage in using quantum dots is that because of the high level of control possible over the size of the crystals produced, it is possible to have very tight control over conductive properties of the material.

As a consequence or selection benefit, quantum dots of the same material, but with different sizes, can emit light of different colors. Quantum dots have distinct optical applications due to their theoretically high quantum yield. In some embodiments, quantum dots of different sizes may be used to select different aptamers or aptamer-plasmid complexes or for aptamer-qdot-nanotube complexes contemplated of use in methods herein. It is appreciated that the selection of quantum dot of use in any of the compositions or methods herein can be optimized depending on the requirements of a particular use.

In other embodiments, a plasmid complex composition may include one or more plasmids with at least one selectable marker and having one or more random aptamers inserted into the plasmid. In other embodiments, a plasmid complex may further include an organic semiconductor associated with the one or more plasmids, wherein the aptamer inserted plasmids and the organic semiconductor forms a plasmid-aptamer-organic semiconductor complex. In other embodiments, plasmid complexes that bind to a target agent through recognition by random aptamers may be selected. Selected plasmid complexes that bind to a target agent may be cloned by introduction to a bacterial or mammalian culture. In addition, aptamers selected from plasmids containing a random aptamer library to bind a target agent may be further associated with an organic semiconductor if grown in a bacterial culture capable of producing organic semiconductors.

Other embodiments for producing plasmid complexes directed to bind a target agent may include, introducing the isolated random aptamer-plasmid constructs associated with the target agent-nanoparticle to a random aptamer-plasmid construct-free bacterial culture, having organic semiconductor synthesis capabilities, to make random aptamer-plasmid construct producing clones; selecting the clones having the selectable marker, wherein the clones having the selectable marker have random aptamer-plasmid constructs associated with the target agent-nanoparticle complexes wherein the random aptamer-plasmid specifically recognizes the target agent. Alternatively, selected clones may be grown on media, wherein the media permits synthesis of organic semiconductors by the clone and wherein the organic semiconductor associates with the selected random aptamer-plasmid constructs making a organic semiconductor-selected random aptamer-plasmid complex capable of targeting the target agent. Organic semiconductor-selected random aptamer-plasmid complex may be further immobilized on a surface.

Single-Walled Nanotubes

In some embodiments, nanotubes may be used to reversibly quench fluorescent agents of some embodiments or complexes disclosed herein. In accordance with these embodiments, nanotubes can be used to quench organic chemical fluors and for example, quantum dots. In addition, carbon nanotubes can be used to directly penetrate cells and deliver nucleic acid molecules that can for example, be recovered by amplification (e.g. PCR). In addition, carbon nanotubes can be used to enhance penetration (e.g. to deliver an agent or compound to the cell or cell nucleus) or destruction of a target cell by for example, radiofrequency to microwave radiation based upon the intensity of the peak E field of the radiation.

Some embodiments of the present invention report using nanotubes as transient quenching agents of fluorescent compounds, for example, for transfection of constructs or agents into cells described herein. In accordance with these embodiments, a nanotube construct may be used in cellular transfection to deliver a targeting molecule (e.g. targeting an agent in a eukaryotic cell for destruction, detection or modification etc.). In certain embodiments, a nanotube construct may be referred to as a nanobe wherein the nanobe includes, but is not limited to a nanoparticle associated with a single-stranded DNA (ssDNA) consensus sequence capable of hybridizing to a complementary sequence, the ssDNA can be associated with a nanotube. In some embodiments, the nanobe complex can penetrate a cell (e.g a eukaryotic cell). In some examples, cells may be transfected in order to modify cells that then in turn modify an organism (e.g. generate non-virulent forms, non-pathogenic forms or the like, generate organisms sensitive to certain types of destruction or to design self-destructing strains or cells etc.).

In other embodiments, a plasmid complex composition disclosed herein may include one or more plasmids or dsDNA with at least one selectable marker, having one or more random aptamers inserted into the plasmid or linked to the dsDNA and a nanotube (e.g. carbon nanotube) associated with the one or more plasmids or dsDNA, wherein the aptamer(s) insert and the nanobe forms a plasmid/dsDNA-random aptamer-fluor-nanobe complex. In certain compositions, a plasmid/dsDNA-random aptamer-fluor-nanobe complex can further include nanoparticles or microbeads, wherein the nanoparticles or microbeads non-covalently associate with the plasmid/dsDNA-random aptamer-fluor-nanobe complex. In other embodiments, plasmid/dsDNA-random aptamer-nanobe complexes that bind to a target agent through recognition by random aptamers may be selected before or after association with nanoparticles or microbeads. Selected complexes that bind to a target agent may be cloned by introduction to a bacterial or mammalian culture. In addition, selected plasmid-random aptamer complexes may further be linked to a nanobe if grown in a bacterial culture capable of producing nanobes. Alternatively, selected plasmid-random aptamer complexes may be linked to a nanobe by synthetic addition of an organic semiconductor to the selected plasmid-random aptamer complexes. In certain embodiments, a complex may be selected that binds to one or more target agents (e.g. a family of target agents or consensus sequences of target agents).

Some embodiments concern carbon nanotube/nanoparticle nanobe (e.g. metallic) where the nanobe is capable of self-assembly. In accordance with these embodiments, an organic semiconductor (e.g. DAT, DALM) can attach to a nanoparticle (e.g. metal) and to DNA (e.g. dsDNA) which, in turn, associates with a carbon nanotube via complementary DNA conjugated covalently to the carbon nanotube. Complexes having a carbon nanotube attached can be transfected into cells where DNA can code for a predetermined protein etc. For example, DNA can code for a nitrate reductase component that acts like an enzyme to synthesize an organic semiconductor (e.g. DALM) in the host cell. This organic semiconductor can interact with DNA or RNA produced by the host cell and can in turn attach to an added metallic nanoparticle (for example, iron that is paramagnetic) and could again attach to an added carbon nanotube, coated with DNA, by complementation. The organic semiconductor/DNA or RNA cell product, by using a disclosed process, can transfer the expressible DNA or RNA to a naïve (or control cell not having the DNA or RNA) host cell via the carbon nanotube associated with it. In addition, a supplementary metallic nanoparticle (e.g. iron) and the carbon nanotube associated with the complex add the capacity to collect the product by a magnet and to add further electromagnetic field interaction (microwave E-field focusing) to the properties of the biosynthetic nanobe for example, for more efficient cellular transfection or, for killing of a predetermined target. In certain embodiments, transfection of a cell by complexes disclosed herein may be tracked or identified based on fluorescence when a complex interacts with a target molecule and the complex is no longer quenched.

In some embodiments, complexes described herein can be used to kill organisms without the need of additional activating agents. In accordance with these embodiments, a complex can include, but is not limited to components of an organic semiconductor-metallic agent-nanotube, wherein the organic semiconductor can coat the nanotube intracellularly to modulate kill of a target organism or cell. In these examples, water can be used as an activator for production and destruction of an organism, eliminating or reducing the need for activating agent(s). An energy source disclosed herein may be used to target the organic semiconductor-coated nanotube for destruction of an organism or cell(s).

Other embodiments of the present invention may concern using nanoparticles or microbeads associated with the selected complexes to immobilize them. Alternatively, target agents may be immobilized on a solid surface and used for selecting aptamer-plasmid complexes that recognize and associate with the target agent. In certain embodiments, the nanoparticles or microbeads associate with the selected complexes covalently or non-covalently. Nanoparticles or microbeads can be, but are not limited to, paramagnetic nanoparticles, quantum dots, nanostructures, colloidal gold, colloidal silver, iron nanoparticles, platinum nanoparticles, microspheres, or nanospheres.

In certain embodiments, target agents may include, but are not limited to, whole organisms such as a virus, bacteria, yeast, spore, metal ions, small organic compounds, biological cofactors, metabolites, proteins, nucleic acids, biological warfare agents, terrorism agents, natural or genetically modified agents. In other embodiments, a target agent may be a protein, peptide, antibody, antibody fragment, polysaccharide, lipid, or nucleic acid.

Samples contemplated herein can be, but are not limited to, samples from a subject such as human samples, mammalian samples, bird samples or reptile samples (e.g. blood, buccal, nasal, tissue, urine, skin). In some embodiments, a sample can be obtained from a domesticated animal for example, a dog, cat, bird or farm animal. It is contemplated herein that a sample may be obtained from a subject having or suspected of developing a disorder and the sample may be screened for the presence or modulation of a target molecule in order for a health professional to assess the subject's condition. Disorders may include, but are not limited to, an infection by bacteria, fungi, virus or the like, or a disorder (e.g. cancer, heart disease, kidney disease, diabetes) or condition (e.g. heart condition, intestinal condition).

In addition, samples reported herein can include one or more samplings from an inanimate object including, but not limited to, air filters, ducts, any surface of an object, such as a counter, wall, a table, a chair, equipment (e.g. military equipment); or any other surface that a subject may come in contact with; or a sample from a food, soil or water source.

Other embodiments may include methods for making and/or using an organic semiconductor-selected aptamer-plasmid complex or nanotube-fluor-dsDNA random aptamer complex capable of binding a target agent. For example, methods may include, but are not limited to obtaining a complex; exposing a sample suspected of having the target agent to the complex; and allowing the complex to bind to the target agent if present in the sample. In certain embodiments of the present invention, a complex may be used to detect, identify or destroy a target agent(s). In accordance with these embodiments, methods may further include, exposing the complex bound to a target agent to an energy source capable of destroying, killing or neutralizing the target agent. Energy sources contemplated herein may include, but are not limited to, microwave radiation, ultraviolet radiation (UV), visible light, laser, electron beam radiation, pulsed corona discharge (non-thermal plasma discharge), other forms of ionizing radiation, and thermal radiation. Other embodiments may include, introducing an attractant to the complex bound to the target agent and concentrating the complex bound to the target agent for further analysis using the attractant to concentrate the target agent.

Other aspects contemplated herein may include a system for detecting an organic semiconductor-selected aptamer-plasmid complex against a target agent. Certain embodiments for a system may include an element for inputting random aptamers in a reaction vessel; and a component for inputting the random aptamers into a plasmid having at least one selectable marker of a first bacterial or first mammalian organism to make random aptamer-plasmid complexes; an element for isolating the random aptamer-plasmid complexes and introducing the random aptamer-plasmid complexes to a second bacterial organism capable of making organic semiconductors in another reaction vessel wherein the organic semiconductor associates with the random aptamer-plasmid complexes; and isolating the organic semiconductor-random aptamer-plasmid complex. Systems for generating random dsDNA aptamer-fluor-nanobes are contemplated.

Other embodiments may include, a system having an aspect for selecting organic semiconductor-random aptamer-plasmid complexes that bind to a target agent. In one aspect, a system using a kit having a lyophilized selectable bacterial culture harboring random aptamer plasmid may be grown up in a media and combined with one or more immobilized target agent(s) then specific aptamer plasmids are selected out by the system using an attractant to immobilized target agent (e.g. magnetic beads). Selectable aptamer-plasmids that recognize the target agent(s) can be isolated and introduced to a naïve culture (e.g. not having a selectable marker) for cloning and isolation by portable means, for example in a remote area. Produced selected aptamer-plasmids that bind and recognize the target agent(s) can be used for any purpose disclosed herein.

Other embodiments may include a kit for making complexes disclosed herein including, but not limited to, a source of fluors, a source of plasmids having at least one selectable marker; a source of random aptamers; and a source for generating organic semiconductors. Other kits contemplated herein may include a source of nanotubes (e.g. SWCNT). A kit may further include magnetic beads or other material capable of attracting and/or concentration nanoparticles. These kits are capable of providing portability for generating a specific molecule of a plasmid-selected aptamer-organic semiconductor complex directed against a target agent of use in a remote or unsophisticated area, for example, in the field.

Example kits may include, but are not limited to, one or more organic semiconductor-selected random aptamer-plasmid complexes capable of binding one or more target molecule able to detect, identify, decontaminate, analyze disease progression, neutralize, determine viability, inactivate, kill or combination thereof. Some kits may contain a partially or completely dehydrated composition including, but not limited to, a bacterial host having a plasmid harboring a random aptamer library or pre-selected aptamer, the host bacterial having the capability of producing organic semiconductors. Alternatively, a kit may include a partially or completely dehydrated composition of a plasmid harboring a random aptamer library or pre-selected aptamer pool capable of being introduced to a bacteria culture for expansion and use. In addition, other kits may include a hydrated or dehydrated composition(s) of random or selected aptamer-fluor-nanotubes complexes for use in embodiments disclosed herein.

In some aspects of the invention, beads or particles contemplated herein can include, but not limited to, paramagnetic beads, magnetic beads, superparamagnetic beads, streptavidin coated beads, Reverse Phase magnetic beads, carboxy terminated beads, hydrazine terminated beads, Silica (sodium silica) beads and IDA (iminodiacetic acid) modified beads, aldehyde modified beads, Epoxy activated beads, DADPA-modified beads (beads with primary amine surface group), biodegradable polymeric beads, amino-polystyrene particles, carboxyl-polystyrene particles, Epoxy-polystyrene particles; dimethylamino-polystyrene particles, hydroxy-polystyrene particles, colored particles, flow cytometry particles, and sulfonate-polystyrene particles. In accordance with these embodiments, a target agent may be covalently or non-covalently linked to a bead or particle. Alternatively, complexes may be immobilized using any bead or particle reported herein.

In certain embodiments, the nucleic acid sequences or aptamers may be sequences of 1 to 1000, 10 to 500, 10 to 250, 10 to 150, 10 to 75, 20 to 60, 15 to 45, 20 to 40 nucleotides or basepairs in length, a single length, a combination of lengths or mixture thereof or combination thereof. In some aspects, a random aptamer library can contain random length aptamers or aptamers of the same or similar lengths may be selected.

In another embodiment, amplification of aptamers (e.g. from a plasmid complex or a nanobe complex) that bind a target agent can be used to generate multiple copies of the aptamers (e.g. DNA), hybrid molecules or RNA aptamers (e.g. RNA aptamers) that bind a target agent. Methods useful for amplifying the partitioned sequences may include, but are not limited to, polymerase chain reaction (PCR™), the ligase chain reaction (LCR) Qbeta Replicase, an isothermal amplification method, Strand Displacement Amplification (SDA), Repair Chain Reaction (RCR), transcription-based amplification systems (TAS), including nucleic acid sequence based amplification (NASBA) and 3SR.

In another embodiment, plasmid complexes may be generated to a target agent and used to analyze the presence of the target agent in a sample suspected of containing the target agent. In accordance with this exemplary use, aptamers directed to bind the target agent can be combined with the sample and the sample can be analyzed for the presence, absence or level of the target agent based on association with the aptamers.

Nucleic Acids

Nucleic acids within the scope may be made by any technique known to one of ordinary skill in the art. Examples of nucleic acids, particularly synthetic oligonucleotides, can include a nucleic acid made by in vitro chemical synthesis using phosphotriester, phosphite or phosphoramidite chemistry and solid phase techniques via deoxynucleoside H-phosphonate intermediates. In certain embodiments, aptamers contemplated herein can be generated and may be modified. Examples of modified aptamers include those that can be modified after amplification reactions such as PCR.™ or the synthesis of oligonucleotides. Examples of a biologically produced nucleic acids include recombinant nucleic acid production in living cells, such as recombinant DNA vector production in bacteria.

Nucleobase, nucleoside and nucleotide mimics or derivatives are well known in the art, and have been described. Purine and pyrimidine nucleobases encompass naturally occurring purines and pyrimidines and derivatives and mimics thereof. These include, but are not limited to, purines and pyrimidines substituted with one or more alkyl, carboxyalkyl, amino, hydroxyl, halogen (i.e. fluoro, chloro, bromo, or iodo), thiol, or alkylthiol groups. The alkyl substituents may comprise from about 1, 2, 3, 4, or 5, to about 6 carbon atoms.

In addition, purine and pyrimidine derivatives or mimics can be used as base substitutions in any of the methods disclosed herein Amplification In certain embodiments, plasmid-aptamer complexes may be amplified to provide a source of high affinity nucleic acids for associating analytes. Amplification may also be of use in the iterative process for generating arrays with greater specificity or binding affinity for a target agent. Within the scope, amplification may be accomplished by any means known in the art.

Primers

The term primer, as defined herein, is meant to encompass any nucleic acid that is capable of priming the synthesis of a nascent nucleic acid in a template-dependent process. Typically, primers are oligonucleotides around 5-100 base pairs in length, but longer sequences may be employed. Primers may be provided in double-stranded or single-stranded form.

In some embodiments, amplification of a random region is produced by mixing equimolar amounts of each nitrogenous base (A, C, G, and T) at each position to create a large number of permutations (e.g. where "n" is the oligo chain length) in a very short segment. This provides dramatically more possibilities to find high affinity nucleic acid sequences when compared to the $10^9$ to $10^{11}$ variants of murine antibodies produced by a single mouse.

A number of template dependent processes are available to amplify the marker sequences present in a given template sample.

In other embodiments, other methods for amplification of nucleic acids, include but are not limited to, the ligase chain reaction ("LCR"), Qbeta Replicase, isothermal amplification methods, and Strand Displacement Amplification (SDA) as well as other methods known in the art. Still other amplification methods may be used in accordance with embodiments disclosed herein. Other nucleic acid amplification procedures may include transcription-based amplification systems (TAS), including nucleic acid sequence based amplification (NASBA). In some of the disclosed methods, the nucleic acid sequences may be prepared for amplification by standard phenol/chloroform extraction, heat denaturation of a clinical sample, treatment with lysis buffer and mini-spin columns for isolation of DNA and RNA or guanidinium chloride extraction of RNA. These amplification techniques involve annealing a primer which has APTAMER specific sequences. Following polymerization, DNA/RNA hybrids are digested with RNase H while double stranded DNA molecules are heat denatured again. In either case the single stranded-DNA is made fully double stranded by addition of second APTAMER specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate APTAMER specific sequences.

Polymerases and Reverse Transcriptases include but are not limited to thermostable DNA Polymerases: OnmiBase™. Sequencing Enzyme Pfu DNA Polymerase Taq DNA Polymerase Taq DNA Polymerase, Sequencing Grade TaqBead™ Hot Start Polymerase AmpliTaq Gold Tfl DNA Polymerase Tli DNA Polymerase Tth DNA Polymerase DNA POLYMERASES: DNA Polymerase I, Klenow Fragment, Exonuclease Minus DNA Polymerase I DNA Polymerase I Large (Klenow) Fragment Terminal Deoxynucleotidyl Transferase T4 DNA Polymerase Reverse Transcriptases: AMV Reverse Transcriptase M-MLV Reverse Transcriptase For certain embodiments, it may be desirable to incorporate a label into the nucleic acid sequences such as the aptamer, amplification products, probes or primers. A number of different labels can be used, including but not limited to fluorophores, chromophores, radio-isotopes, enzymatic tags, antibodies, chemiluminescent, electroluminescent, and affinity labels. Examples of affinity labels contemplated herein, can include, but are not limited to, an antibody, an antibody fragment, a receptor protein, a hormone, biotin, DNP, and any polypeptide/protein molecule that binds to an affinity label.

Examples of enzymatic tags include, but are not limited to, urease, alkaline phosphatase or peroxidase. Colorimetric indicator substrates can be employed with such enzymes to provide a detection means visible to the human eye or spectrophotometrically visible.

The following fluorophores disclosed herein can include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Solid Phase

It is contemplated herein that any solid phase support may be used for isolation or immobilization of a separated target agent or aptamer-plasmid complex of any of the procedures disclosed herein. In some embodiments, a solid phase component can include beads or a bead technology for example beads, microbeads, particles, microparticles, nanoparticles or combination thereof. In accordance with these embodiments, the beads or particles may be selected from the group consisting of paramagnetic beads, magnetic beads, superparamagnetic beads, streptavidin coated beads, Reverse Phase magnetic beads, carboxy terminated beads, hydrazine terminated beads, Silica (sodium silica) beads and IDA (iminodiacetic acid) modified beads, aldehyde modified beads, Epoxy activated beads, DADPA-modified beads (beads with primary amine surface group), amino-polystyrene particles, carboxyl-polystyrene particles, Epoxy-polystyrene particles, dimethylamino-polystyrene particles, hydroxy-polystyrene particles, colored particles, flow cytometry particles, sulfonate-polystyrene particles or combination thereof.

Methods of Immobilization of Amplified Aptamers or Target Molecules

In various embodiments, amplified population of aptamer-plasmid complexes may be attached to a solid surface ("immobilized"). In other embodiments, target molecules associated with nanoparticles may be associated with a solid surface. In one embodiment, immobilization may occur by attachment of an organic semiconductor to a solid surface, such as a magnetic bead, a plastic microtiter plate or a glass slide or a chip material. In one example, use of a semiconductor for this system is advantageous in that the attachment of aptamers may be readily reversed by addition of a chelator, such as EDTA if the attachment is through magnesium or some other chelatable compound.

Immobilization of aptamers may alternatively be achieved by a variety of methods involving either non-covalent or covalent interactions between the immobilized aptamers, for example, an anchorable moiety, and an anchor. In some embodiments, immobilization may be achieved by coating a solid surface with streptavidin or avidin and the subsequent attachment of a biotinylated polynucleotide. Immobilization may also occur by coating a polystyrene or glass solid surface with poly-L-Lys or poly L-Lys, Phe, followed by covalent attachment of either amino- or sulfhydryl-modified polynucleotides, using bifunctional crosslinking reagents by methods known in the art.

Other solid surfaces contemplated of use may include, but are not limited to, glass, plastic, silicon-coated substrate, macromolecule-coated substrate, particles, beads, microparticles, microbeads, dipstick, magnetic beads, paramagnetic beads and a combination thereof. In certain embodiments, these solid surfaces can be used to immobilize an amplified aptamer for further use such as detecting an analyte or agent in a sample.

Immobilization may take place by direct covalent attachment of short, 5'-phosphorylated primers to chemically modified polystyrene plates. The covalent bond between the modified oligonucleotide and the solid phase surface is formed by condensation with a water-soluble carbodiimide. This method facilitates a predominantly 5'-attachment of the oligonucleotides via their 5'-phosphates. In addition, attachment to a solid surface may be made through non-covalently immobilizing aptamer molecules in the presence of a salt or cationic detergent on a hydrophilic polystyrene solid support containing an —OH, —C=O or —COOH hydrophilic group or on a glass solid support. The support is contacted with a solution having a pH of about 6 to about 8 containing the aptamer and the cationic detergent or salt. The support containing the immobilized aptamer may be washed with an aqueous solution containing a non-ionic detergent without removing the attached molecules.

One commercially available method for immobilization is the "Reacti-Bind™ DNA Coating Solutions" (see Instructions—Reacti-Bind.™ DNA Coating Solution). This product comprises a solution that is mixed with DNA and applied to surfaces such as polystyrene or polypropylene. After overnight incubation, the solution is removed, the surface washed with buffer and dried, after which it is ready for hybridization. It is envisioned that similar products, i.e. Costar "DNA-BIND™" or Immobilon-AV Affinity Membrane (IAV, Millipore, Bedford, Mass.) may be used in the practice of the embodiments disclosed herein.

Separation and Quantitation Methods

In some embodiments, it may be desirable to separate aptamers of a clone of different lengths for the purpose of quantitation, analysis or purification. In other embodiments it may be desirable to separate aptamers of a clone and group them by size in order to use them for methods disclosed herein.

Gel Electrophoresis

In one embodiment, aptamers of an aptamer-plasmid clone (e.g. target agent directed) can be sized by for example, excising the aptamer of interest and using agarose, agarose-acrylamide or polyacrylamide gel electrophoresis or other methods known in the art for sizing an insert.

Separation by electrophoresis is based upon methods known in the art. Samples separated in this manner may be visualized by staining and quantitated, in relative terms, using densitometers which continuously monitor the photometric density of the resulting stain. The electrolyte may be continuous (a single buffer) or discontinuous, where a sample is stacked by means of a buffer discontinuity, before it enters the running gel/running buffer.

Chromatographic Techniques

Alternatively, chromatographic techniques may be employed to effect separation. There are many kinds of chromatography which may be used for example: adsorption, partition, ion-exchange and molecular sieve, and many specialized techniques for using them including column, paper, thin-layer and gas chromatography.

Aptamers Combinational Uses

Random aptamers may be prepared by any method known in the art. In addition, aptamers or aptamer-plasmid clones may be used alone or in combination with other aptamers or other aptamer-plasmid clones specific for the same or different target agents. Further, aptamers may specifically include "secondary aptamers" where a consensus sequence is derived from comparing two or more isolated aptamers or aptamer-plasmid clones that bind to a given target.

In general, a minimum of approximately 3 nucleotides, preferably at least 5 nucleotides, can effect specific binding.

The binding specificity of the target/agent capture element complexes disclosed herein concern sufficient sequence to be distinctive in the binding aptamers and sufficient binding capacity of target agent(s) to obtain the necessary interaction. Oligonucleotides of sequences shorter than 10 bases can be feasible if interaction can be obtained in the context of the environment in which the target is placed.

Any aptamer or aptamer-plasmid contemplated herein can contain a sequence that confers binding specificity, but may be extended with flanking regions and otherwise derivatized. In one particular embodiment, aptamer binding sites can be flanked by known, amplifiable sequences, facilitating the amplification of the aptamers by PCR or other amplification techniques. In a further embodiment, flanking sequence(s) may include a specific sequence that recognizes or binds a moiety to enhance the immobilization of an aptamer to a substrate.

Aptamers of interest may include modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. The 5' terminal OH is conventionally free but may be phosphorylated. Hydroxyl group substituents at the 3' terminus may also be phosphorylated. The hydroxyls may be derivatized by standard protecting groups. One or more phosphodiester linkages may be replaced by alternative linking groups. These alternative linking groups include, exemplary embodiments wherein P(O)O is replaced by P(O)S, P(O)NR$_2$, P(O)R, P(O)OR', CO, or CNR$_2$, wherein R is H or alkyl (1-20 C) and R' is alkyl (1-20 C); in addition, this group may be attached to adjacent nucleotides through O or S, Not all linkages in an oligomer need to be identical.

Aptamers generated or used as starting materials in a process may be single-stranded or double-stranded DNA. In some embodiments, sequences are double-stranded DNA. In some embodiments, aptamers will contain a randomized sequence portion, generally including from about 10 to 400 nucleotides, more preferably 20 to 100 nucleotides. Randomized sequences can be flanked by primer sequences that permit the amplification of aptamers found to bind to a target agent. Flanking sequences may also contain other features, such as restriction sites. These primer hybridization regions can contain for example 10 to 80, or 15 to 40, or 20 to 40, bases of known sequence. Randomized portions and primer hybridization regions of the initial oligomer population are preferably constructed using conventional solid phase techniques. Such techniques are well known in the art. Aptamers may also be synthesized using solution phase methods such as triester synthesis, known in the art. For synthesis of some randomized regions, mixtures of nucleotides at positions where randomization are desired are added during synthesis.

Any degree of randomization may be employed. Some positions may be randomized by mixtures of only two or three bases rather than the conventional four. Randomized positions may alternate with those which have been specified. Indeed, it is helpful if some portions of the candidate randomized sequence are in fact known.

In some embodiments, substrates may be used for immobilization of bacterial cultures harboring plasmids disclosed herein. Substrates for immobilization may include, but are not limited to, nitrocellulose, nylon membrane or glass. Numerous other matrix materials may be used, including, but not limited to, reinforced nitrocellulose membrane, activated quartz, activated glass, polyvinylidene difluoride (PVDF) membrane, polystyrene substrates, polyacrylamide-based substrate, other polymers such as poly(vinyl chloride), poly (methyl methacrylate), poly(dimethyl siloxane) and photopolymers which contain photoreactive species such as nitrenes, carbenes and ketyl radicals capable of forming covalent links with target molecules.

It is contemplated herein that any of the aptamers used in compositions or methods can be one specific aptamer or a mixture of aptamers directed to one or more target agent.

EXAMPLES

The following examples are included to demonstrate some embodiments. It should be appreciated by those of skill in the art that the techniques disclosed in the examples which follow represent techniques discovered by the inventors to function well in the practice of embodiments disclosed herein, and thus can be considered to constitute exemplary modes for its practice. However, those of skill in the art should, in light of some embodiments, appreciate that many changes can be made in certain embodiments which are disclosed and still obtain a like or similar result without departing from the spirit and scope herein.

Example 1

BioSPLICE is the acronym for Biosynthetic plasmid integrated capture element. It represents the culmination of basic and applied research to solve the problem of generating a biological system that can detect, identify and neutralize target biological agents in a seamless manner. The final BioSPLICE system is self-contained, self-replicating and capable of performing the aforementioned functions without extensive reagents or instrumentation. The system has a number of options for reporting and neutralizing the target biological agent that can incorporate sophisticated external instrumentation (e.g. Charles River Device, PNNL Green Box, GE DVD Device, GE RFID concept device, microtiter plate reader for visible light absorption or fluorescence, or a luminometer for thermochemiluminescence for "reading" reporters; and cold plasma, pulsed microwave devices or UV A or visible light irradiatiors for neutralization) or employ the simplest physical and chemical means (color or color intensity change, visible to the eye, when bound to a target agent or activation of bound reporter with hydrogen peroxide and bicarbonate for killing with heat or sunlight). This system is versatile and flexible. BioSPLICE can be used to select new targeting elements in the field and retain this new signature for further replication and utilization and still provide biologically encoded information that can be sent reported.

Example 2

In one exemplary method, compositions (e.g. BioSPLICE methodologies) involve generating and using recombinant plasmid vectors containing a DNA aptamer insertion(s) (DNA Capture Element) in the host bacterium species/strain (e.g. *Escherichia coli* JM109 or HB101) or a mammalian cell. This plasmid can be extracted and bound specifically to a molecular target (e.g., protein, polysaccharide, lipid, or nucleic acid) where the target molecule is immobilized covalently or non-covalently on a paramagnetic metallic nanoparticle. The binding can occur prior to or after plasmid extraction because such nanoparticles can penetrate living microbes or cells. If random collections of aptamers are present as plasmid inserts, the one that binds best to the molecular target linked to a nanoparticle will be selected and isolated. After magnetic separation of the nanoparticles of the better or best binding aptamers, they are added to a parent *E. coli* that does not contain the plasmid and is, in certain cases, not resistant to ampicillin, another antibiotic or selectable marker to which the plasmid conveys resistance.

After sufficient incubation time for the bacteria (e.g. *E. coli*) to take up the plasmid-coated nanoparticles (uncoated nanoparticles will also be taken up), the bacteria are plated on solid media (agar) or on a media impregnated filter containing ampicillin alone or LB agar plates with ampicillin. Only cells that successfully bound the plasmid-coated nanoparticles through the aptamer-molecular target link and transferred an expressible plasmid to the recipient parental host will grow on the ampicillin medium. The surviving clones can be selected and amplified by further culturing in medium. DNA can be extracted from this culture and the aptamer can be cut out of the plasmid and sequenced to reveal the specific aptamer selected. When these surviving clones are grown on 3-AT medium, they will produce an organic semiconductor (e.g. diazoluminomelanin (DALM)) which will be biosynthetically linked through the plasmid DNA containing the specific aptamer to the target microbe. The complex can be incubated with a target molecule-containing sample. Then, activation with ultraviolet (UVA or UVB) light, sodium bicarbonate and hydrogen peroxide and heat or microwave energy, the target molecule will be killed or neutralized. Alternatively, these DALM/plasmid/aptamer complexes can be used also to detect and identify the target microbe by specific binding detected by thermochemiluminescence, slow fluorescence, visible light absorption, or colorimetric means. The magnetic property of the nanoparticles, which bind non-covalently to the DALM/plasmid/DCE, can be used to concentrate the complex bound to the target for detection, identification, or further analysis. Finally, the DALM/plasmid/aptamer complex can be used to target the free-radical destruction of target agent facilitated by microwave radiation, UV and visible light, heat, and chemical agent exposure.

Example 3

In another exemplary method, freeze-dried seed stock library of 1MI 09/pIC20R NR1.1DCE (*E. coli* host containing a library of random aptamer/DCE sequences in the plasmid with the genes for ampicillin resistance and the capability to make organic semiconductor) can be grown up in liquid growth medium using the standard portable field incubator used currently in the USAF for water quality assessment (coliforms), This culture would form the stock of plasmid, following lysis with a lysis solution, for selecting the new DNA aptamer sequences for a biological agent discovered in the field. The biological agent source of interest would then be mixed with metallic nanoparticles that chemically (covalently or non-covalently) link to molecular targets on the surface of microbes or directly to molecular-scale toxins. These would be "purified", extracted from the milieu, and separated by an attractant such as a magnet. The collected nanoparticle bound target would then be washed several times with water or buffer and then lysed with a lysing buffer or solution (similar to what was used for the library bacteria). This latter process would kill and break up the agent but leave the molecular target bound to the nanoparticle, The nanoparticles would then be magnetically extracted (same as above) and washed with a solution compatible with the binding of the plasmid/DCE. This preparation would then be added to a re-constituted culture of freeze-dried JMI 09 parent (lacking plasmid). After the appropriate time, the bacteria would be deposited on a culture filter (similar to those used in the standard water quality assay) and placed over a sponge containing the ampicillin-containing culture medium. This preparation is then incubated in the portable incubator until colonies appear on the filter grid. Isolated colonies can be picked off with a sterile swab or loop and transferred to culture medium for expanding the clones. These clones are the ones that will make DCE against the new target on demand if they are grown in 3AT liquid medium in the portable incubator and the DALM/plasmidIDCE is extracted into the supernatant (just the spontaneous lysate are left when the solids fall out of solution or are frozen out), this crude supernatant can be used to detect, identify and sensitize the target biological to killing as mentioned above. Also, the DNA from this supernatant contains the sequence 'fingerprint' that can be dried and sent for further analysis such as sequencing.

Example 4

Some advantages of the embodiments herein are that selected aptamers of the selected plasmid-random aptamers are a signature of a target molecule of interest. The sequence may match or show homology to one in a database of aptamer sequences or it can be used to against known agents supporting laboratories to validate identification without the need to transport a target the agent from the field. Therefore, the DCE/aptamer is selected and manufactured in the field in the forward area for use against a particular agent. All the reagents (mostly media and lysis solution components) can be kept in un-refrigerated freeze-dried packaged form to be reconstituted with water. The cultureware can be plastic and disposable and carried in a cooler-sized portable incubator. Pre-placed freeze-dried seed stocks against a given agent can be placed in the field for manufacture of detecting, identifying and neutralizing DCEs, similar to what is described above for selecting DCEs for unknown agents. The non-specific linking of the nanoparticles to the surface of an intact agent before the lysing of the microbe also tends to select molecular targets on the microbe that are accessible and associated with a living or viable agent, other than culture, no existing binding method can determine agent viability.

Example 5

An alternative selection method would be uptake of nanoparticles coated with a molecular target into a living microbe or cell in order for binding to the aptamer to occur intracellularly. After binding, the microbe or cell is lysed and the nanoparticle with the attached aptamer is magnetically extracted. It is then added to a new parent microbe or cell which is selected by the antibiotic resistance marker on the plasmid when successfully incorporated. The same approach as above can be applied to mammalian cells. Methods and compositions of plasmids and vectors for placing and expressing organic semiconductor-producing gene in animal and human cells and this plasmid could potentially harbor the DCEs. Also, it contains a neomycin-resistance gene that is expressed and allows for the selection of gene recombinants in these cells. An *E. coli* HB101 host, containing this vector plasmid pSV2neoNR1 OI (American Type Culture Collection #69617; U.S. Pat. No. 5,464,768), can be used to carry and propagate the DCE inserts. This host and plasmid could be used to produce the DCE clones against a specific biological agent as described above. Then, the selected plasmids could transferred to a parent HB101 for further propagation of the plasmid and/or transfected by the same nanoparticle carrier technique into a host animal or human cell for the production of DALM and DCEs that would be specifically directed against an intracellular target, through DCE/DALM/DNA, or the RNA/DALM counterpart's binding and microwave radiation activation of neutralization. The DNA DCEs would be converted into RNA, previously selected against a target, or by transcription of the RNA (intracellular) to be selected for binding to intracellular targets. Thus, the DCEs in the plasmids would be cDNA of the actual RNA aptamers that would attach to the target (data not shown). DALM/DCE plasmids can successfully transfect parental JM109 and HB101 strains of *E. coli*. Second generation transfection of parental *E. coli* with the initial transfectants' DALM/DCE plasmids has been successfully completed (data not shown).

FIGURES

FIG. 1 represents interactions between nanoparticles, DNA and organic semiconductors.

FIG. 2 illustrates plasmid generation and transfer (200) of some embodiments disclosed herein. In this schematic, 202 represents a plasmid with aptamer (DCE) and nitrate reductase and ampicillin resistance genes for DALM production and clonal selection, respectively; 203 represents bacterial chromosome; 204 represents DALM nanobe "coat" and 201 represents a host microbe for synthesizing random aptamer or select aptamer-plasmid complexes.

A pIC plasmid vector can be represented. The Taq1 site is used as a reference point. (at 4018 of pBR322). The other Taq1 sites are located between Hind III and the polylinker. Other sites are shown for insertion of a selected aptamer or random aptamer library.

FIG. 3 illustrates an exemplary eukaryotic nanobe, RAW 264.7 cells making DALM structures is represented. In this figure, 300, 305 represents the nucleus; 312 represents DNA; 306 represents mRNA; 307 represents NR (nitrate reductase); 310 represents DALM; 308 represent aptamer RNA; 303 represents DALM; 302 represents NP (metallic nanoparticle); and 301 represents a bacterial host and 311 represents release and binding of the aptamer-DALM complex 308/310 to intracellular targets or those in or on other cells.

FIG. 4 illustrates an example of isolation and electrophoretic separation of DNA fragments of Nitrate Reductase presence in HK2 cells after exposure to synthetic DALM coated nanobe.

FIG. 5 illustrates a schematic of aptamer selection and nanobe replication in a remote area the star represents immobilized or captured agent; 501 represents aptamer-plasmid complex; 503 represents a nanoparticle; 502 represents DALM; 505 represents a bacterial host and 504 represents replication of a plasmid-selected aptamer after isolation and introduction to a host for replication.

Materials and Methods

Some embodiments may include using one or more of the experimental methods outlined below.

DALM Production

Solutions:

Luria Bertani (LB) agar plates: dissolve 1 LB agar tablet (Sigma-Aldrich, L7025) per 50 mL dH2O. Autoclave at 121° C. for 15 min. Once cooled, pour the LB/AMP agar into 100 mm×15 mm petri-dishes (Fisher, MS-D13-00325), let solidify and store at 4° C.

LB/Ampicillin (AMP) agar plates: dissolve 1 LB agar tablet per 50 mL dH2O. Autoclave at 121° C. for 15 min. Once agar reaches 40° C., replace 30 μL per 100 mL LB broth with 30 μL of 100 mg/mL AMP (Sigma Aldrich, A8511) stock to make [30 μg/mL]. Pour the LB/AMP agar into 100 mm×15 mm petri-dishes, let solidify and store at 4° C.

Tryptic Soy Broth (TSB): dissolve 15 g of Tryptic Soy Broth (MP, 101717) into 500 mL dH2O and autoclaved at 121° C. for 15 minutes (min.). Once cooled, store at 4° C.

4×3AT MEDIA: In 4 separate 2 L glass flasks and 1 L glass bottle make 1 liter solutions of 60 mg/L of 3-Amino-L-Tyrosine dihydrochloride (Sigma-Aldrich, A9383), 6 g/L of potassium nitrate (Fisher, BP368-500), 50 mg/L of Luminol (Sigma-Aldrich, A8511) and 30 g/L of TSB. Autoclave at 121° C. for 15 min. When media cools to 40° C., replace 300 µL of media in flasks with 300 µL of 100 mg/mL AMP stock to make a [30 m/mL]. When 1 L bottle cools, store at 4° C. The following procedure may be used: Streak strains of OAJ 6, 7, 8 and JM109pIC (all containing the AMP resistant plasmid insert NR1.1) onto separate LB/AMP agar plates using 1 µL inoculating loops (Fisher, 14-906-29). Streak JM109 parental strain (no NR1.1 plasmid insert) onto an LB agar plate and an LB/AMP plate (as a negative control validation). Place plates in a 37° C. incubator overnight. After overnight incubation, observe plates for growth. There should be no growth of JM109 parental strain on LB/AMP plates. Then, Pipet 12 mL of TSB in a 15 mL conical Falcon tube (Fisher, 14-959-70C). Replace 3.64, of media with 3.64, of 100 mg/mL AMP stock. After vortexing, pipet 3 mL into 4 separate 5 mL snap cap tubes (Fisher, 14-959-2A). Pick clones of OAJ 6, 7, 8 and JM109pIC from LB/AMP plates and inoculate into each properly labeled, respective 5 mL snap cap tube and place slanted in 37° C. incubator shaker overnight. Pour liquid cultures into properly labeled and respective 2 L flasks containing 4×3AT media/AMP. Cover each flask cheesecloth squares (Fisher, AS-240) secured with tape and loosely cover with foil secured with tape onto flask as well. Place all 4 flasks into 37° C. shaker incubator for 5 days. After about 5 days time period, make 5 mL aliquots in 15 mL conical Falcon tubes, labeled accordingly (OAJ 6, 7, 8 and JM109pIC) and place in −20° C. freezer overnight. Once solidified, a top layer is observed in the 15 mL conical Falcon tubes. Open tubes and invert onto petri-dishes. Only the top layer is allowed to melt and collect in the petri-dishes while the remaining contents of the 15 mL tube are properly discarded. Collect the top layer, synthesized DALM, into separate 50 mL conical Falcon tubes (Fisher, 14-959-49A), properly labeled OAJ6, OAJ7, OAJ8 or JM109pIC, cover with foil and store at 4° C.

Coating Nanoparticles (Fe) with DALM Cocktail

In some embodiments, nanoparticles may be coated with an organic semiconductor. In one example, nanoparticles are coated with DALM. A stock of nanoparticles, 12.5 µL of [10 µg/µL] stock of various nanopaticles (Fe, Ag, FeAgC and FeC), is mixed with 500 µL DALM cocktail in respective 2.0 mL microcentrifuge tubes. Then, wrap each tube in foil and allow to incubate at 4° C. with constant rotation overnight. After overnight incubation, use a magnetic microcentrifuge chamber to separate the nanoparticles from the DALM. With the nanoparticles collected on one side of the tube, extract the 500 µL DALM carefully from the tube using a transfer pipet and replace it with 500 µL of dH2O. Reconstitute the nanoparticles in the 500 µL dH2O by vortexing. Repeat wash steps twice more for each tube to ensure the nanoparticles are washed completely. After the final extraction of dH2O, wrap tube in foil and store at 4° C. until needed.

JM109 Parental Strain Exposed to DALM-Coated Fe Nanoparticles (DCFe)

Solutions: Fe nanoparticles (NP)—using proper PPE, weigh out 100 mg of 15 nm Fe NP (e.g. Nanotechnologies, Fe-15-ST2, M19003) and suspend in 10 mL of chilled dH2O in a glass scintillation vial (Research Products Int'l, 3002-1RP). Make [10 µm/µL] stock solution. Directly sonicate (Branson Sonifier, Model 250) solution for 5 minutes in 1 minute intervals to keep NP in solution. Store at 4° C.

DALM cocktail—combine 300 µL of each strain of synthesized DALM into a 5 mL snap cap tube.

LB Broth—place 1 LB broth tablet (Sigma-Aldrich, L7275), per 50 mL of dH2O. Autoclave at 121° C. for 15 min. Store at 4° C.

LB/AMP Broth—Replace 30 µL per 100 mL LB broth with 30 µL of 100 mg/mL AMP stock to make [30 µg/mL] concentration. Make 12-10 µL aliquots of Fe NP stock solution in separate 0.5 mL microcentrifuge tubes (USA Scientific, 1605-0000) and store in 4° C. After vortexing the DALM cocktail, pipet 200 µL into 4 of the Fe NP aliquot stocks. Cover the tubes with foil, place on a rotator and incubate at 4° C. overnight. After Fe NP are coated with DALM cocktail, uncover tubes and wash three times with dH2O using a magnetic microcentrifuge tube holder (Dynal). Once washed, pipet 200 µL of LB broth into tubes and vortex. Label 4-15 mL conical Falcon tubes JM109 1DCFe and fill with 4.8 mL of LB broth. Pipet 200 µL of LB/DCFe NP in microcentrifuge to 15 mL tubes and vortex. Pick a clone of JM109 parental from LB agar plate and inoculate each 15 mL Falcon tube. Loosely cover the tubes and place slanted in 37° C. shaker incubator for 12-16 hr. Streak 1 mL of each liquid culture in 200 µL aliquots onto LB/AMP plates and incubate at 37° C. overnight. Pick 4 clones from LB/AMP plates and inoculate 5 mL LB/AMP broth in separate properly labeled 15 mL conical Falcon tubes. Loosely cover the tubes and place slanted in 37° C. shaker incubator for 12-16 hr. Also, pipet 5 mL LB/AMP broth into properly labeled 15 mL conical Falcon tubes and inoculate separate clones of OAJ6, OAJ7, OAJ8 and JM109pIC. Loosely cover the tubes and place slanted in 37° C. shaker incubator for 12-16 hr.

DNA Extraction: Boiling Miniprep

Solutions: STET: for 200 mL; 16 g sucrose (Sigma, S1174), 10 mL 1M TrisCl (??), pH 8.0, 20 mL 500 mM EDTA (Invitrogen, 15575-020), 10 mL Triton X-100 (Sigma, T9284) and add dH2O to 200 mL. Filter sterilized and stored at 4° C.

Lysozyme: 10 mg Lysozyme powder (Sigma-Aldrich, L-7651) dissolved in 1 mL TE (Invitrogen, 12090-015). Make fresh each time and kept on ice until used. 8M ammonium acetate: 61.66 g of ammonium acetate (Sigma, A1542) dissolved qs to 100 mL dH2O. Filter sterilized and stored at room temperature (temp). Ammonium acetate/isopropanol: 5 volumes of 8M ammonium acetate to 12 volumes of Isopropanol (Sigma, 19030). Mix and store in sterile bottle at room temp. Do not autoclave solution. 70% ethanol: Mix 70 mL absolute ethanol and 30 mL dH2O. Store in sterile bottle at 4° C.

After vortexing LB/AMP liquid cultures grown overnight, transfer 2.0 mL into separate, properly labeled 2.0 mL microcentrifuge tubes (Fisherbrand, 05-408-138) and centrifuge (Eppendorf Centrifuge, 5417R) at 5000 rpm for 4 minutes. A blank with 2 mL of dH2O will also need to be made. Aspirate supernatant and pipet 300 µL of STET to pellets in tubes and vortex to reconstitute cells in solution. Add 25 µL of Lysozyme solution into each tube and vortex. Immediately transfer tubes to 100° C. heating block for 2 minutes. Centrifuge tubes at 16400 rpm for 5 minutes at room temperature. Discard loose pellet using a sterile inoculating loop and add 300 µL of ammonium acetate/isopropanol solution to the supernatant in each tube and vortex. Centrifuge tubes at 14000 for 5 minutes at room temperature. Pour off supernatant and blot tubes on paper towel. Add 500 µL of 70% ethanol to pellet, vortex and centrifuge tubes at 16400 rpm for 5 minutes at room temperature. Pour off supernatant and blot tubes on paper towel and allow pellet and tube to completely dry before adding 50 μL of TE buffer.

DNA Extraction: Spin Preparation

Qiaprep Spin: Overnight liquid cultures (1.5 mL of the 2 mL) were transferred to respective 2 mL microcentrifuge tubes (USA Scientific, 1480-2700) and centrifuged a 8000 rpm for 3 min (Eppendorf, Centrifuge 5417R. After the tube was inverted 4 times, 350 μL of Buffer N3 was mixed immediately and thoroughly by inverting the tubes 4 times. The tubes were centrifuged for 10 min at 13,000 rpm. The supernatant of each tube was then transferred to the QIAspin column by decanting and centrifuge for 1 min at 13,000 rpm. After the flow-through was properly discarded, the columns were washed with 500 μL of Buffer PB and centrifuged for 1 min at 13,000 rpm. The columns were washed with 750 μL of Buffer PE and centrifuged for 1 min at 13,000 rpm. The tubes were centrifuged for 1 min at 13,000 rpm to remove any residual wash buffer. The columns were transferred to a clean 2.0 mL microcentrifuge tube and 50 μL of buffer EB was added. The columns were allowed to stand for 1 min before being centrifuged for 1 min at 13,000 rpm. The DNA was then properly stored in −20° C. freezer until needed.

In one example, fragments of interest may be amplified and detected. In this example, NR1.1 was amplified and isolated.

Detection via PCR and Electrophoresis

PCR Master Mix: 5 μL—10×PCR Rxn Buffer (e.g. Invitrogen, Y02028); 2 μL—50 mM MgCl2 (e.g. Invitrogen, Y02016); 1.3 μL—5% DMSO (e.g. Sigma, D2650); 1 μL—dNTP (e.g. Atlanta Biologicals, 362275); 0.4 μL—Taq polymerase (e.g. Invitrogen, 18038-042), added last 20.3 μL—dH2O nuclease free (e.g. Gibco, 10977-015); 2.5 μL—NR1.1F primer (e.g. Sigma-Genosys, 37998580-010); and 2.5 μL—800R primer (e.g. Sigma-Genosys, 37998580-020). Add 33 μL of Master Mix to properly labeled PCR tubes (e.g. Fisher, 08-408-229) containing 10 μL of respective DNA extraction samples. For PCR in a thermocycler (e.g. Biometra, T3000) as follows: 40 cycles Lid Temperature—103° C. Temperature 94° C.—10 min. Temperature 94° C.—45 sec. Temperature 55° C.—35 sec. Temperature 72° C.—2 min. Temperature 72° C.—5 min. Temperature 4° C.—pause. Make a 1.5% agarose gel as follows: dissolve 1.5 g of pure agarose (e.g. Invitrogen, 15510-027) into 100 mL of 1×TAE Buffer (e.g. BioRad, 161-0743). Heat in microwave on high for 1 minute and observe agarose is completely dissolved. Pour agarose/1×TAE into gel canister (e.g. BioRad) in gel mold (e.g. BioRad) with combs (e.g. BioRad) and set aside until solidified. Once PCR is complete, pipet 5 μL of SYBR Gold (e.g. Invitrogen, S11494) and 5 μL of sample into a separate, respective PCR tube. For Ladder (e.g. Fermentas, SM1373): pipet 5 μL SYBR Gold and 2 μL of Ladder. Carefully pipet all contents of each tube into respective well and run electrophoresis unit (BioRad, Model 200) for 70V for 30 minutes. View gel using UV light source (Syngene, G-Box) and observe 1.1 kb bands (e.g. NR1.1).

Synthesis of 1st Generation Transformation DALM

Streak 1 mL of each remaining JM109 DCFe (DALM coated iron nanoparticle) liquid cultures onto properly labeled and respective LB/AMP agar plates in 200 μL aliquots and incubate at 37° C. Pipet 12 mL of TSB in a 15 mL conical Falcon tube and replace 3.6 μL of media with 3.6 μL of 100 mg/mL AMP stock. After vortexing, pipet 3 mL into 4-5 mL snap cap tubes. Pick 4 clones from LB/AMP agar plates and inoculate the 4-5 mL snap cap tubes containing TSB/AMP. Place tubes slanted in 37° C. shaker incubator overnight. In 4-250 μL glass flasks, pour 100 mL of 4×3AT media and replace 30 μL of media with 30 μL of 100 mg/mL AMP stock to make [30 μg/mL]. Pour TSB/AMP liquid cultures into a separate flask containing 4×3AT/AMP and cover flasks with cheesecloth squares secured with tape and loosely cover with foil secured with tape. Place flasks in 37° C. shaker incubator for 2-3 days. After incubation period, make 5 mL aliquots in 15 mL conical Falcon tubes, labeled accordingly (e.g. JM109 DCFe) and place in −20° C. freezer overnight. Once solidified, a top layer is observed in the mL conical Falcon tubes. Open tubes and invert onto Petri-dishes. Only the top layer is allowed to melt and collect in the petri-dishes while the remaining contents of the 15 mL tube are properly discarded. Collect the top layer, synthesized DALM, into a 50 mL conical Falcon tubes labeled JM109 1DCFe DALM, cover with foil and store at 4° C.

JM109 Parental Strain Exposed to DCFe of 1St Generation Transformation

Figure 6:
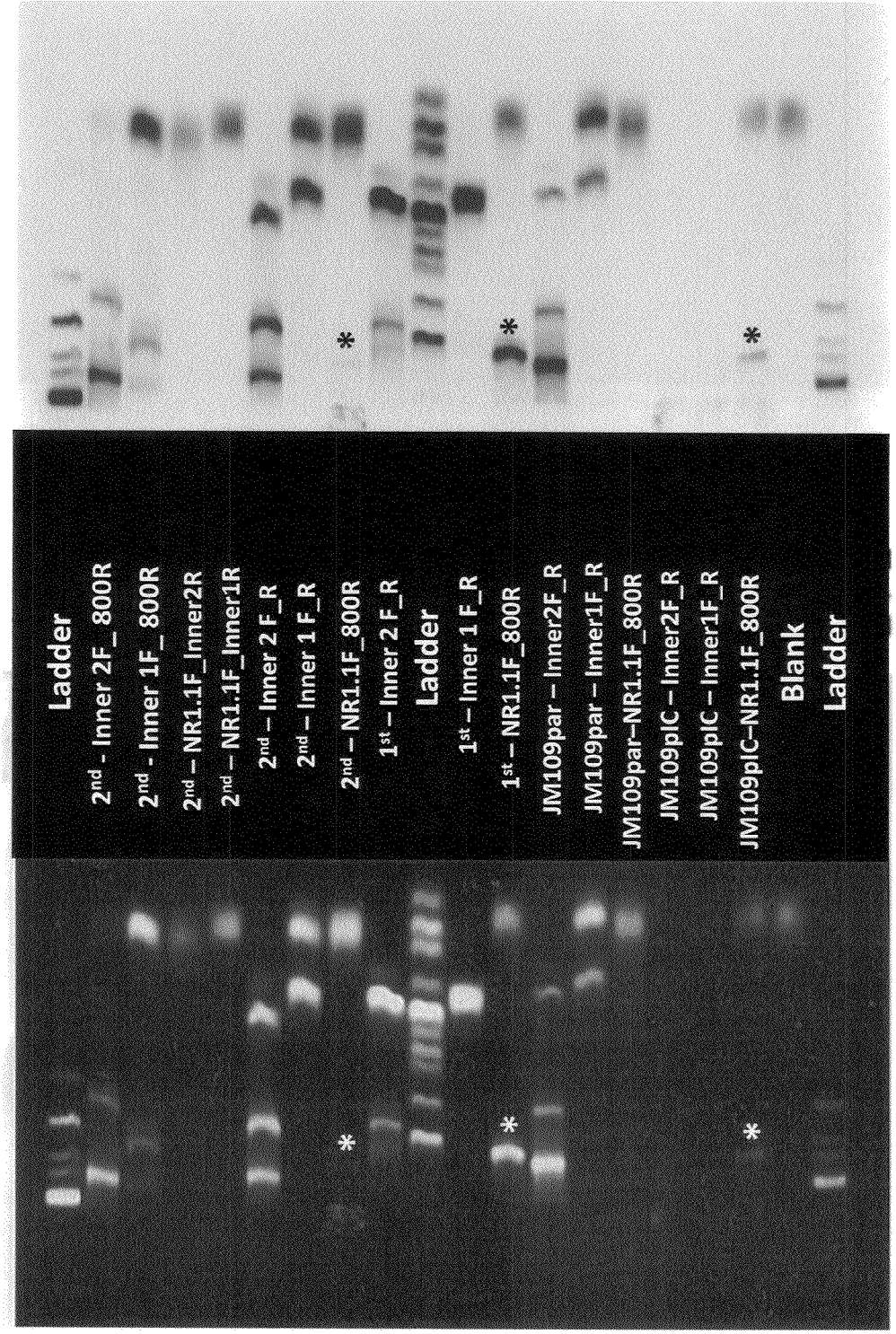
FIG. 6 represents an exemplary electrophoresis gel illustrating presence or absence of a predetermined insert (as shown by asterisk (*)), standards were included in the gel.

Obtain (e.g. 4) Fe NP aliquot stocks and pipet 200 μL of JM109 1DCFe DALM into each microcentrifuge tube, cover with foil, place on a rotator and incubate overnight at 4° C. After Fe NP are coated with DALM cocktail, uncover tubes and wash three times with dH2O using a magnetic microcentrifuge tube holder. Once washed, pipet 200 μL of LB broth into tubes and vortex. Label 4-15 mL conical Falcon tubes JM109 2DCFe and fill with 4.8 mL of LB broth. Pipet 200 μL of LB/DCFe NP in microcentrifuge to 15 mL tubes and vortex. Pick a clone of JM109 parental from LB agar plate and inoculate each 15 mL Falcon tube. Loosely cover the tubes and place slanted in 37° C. shaker incubator for 12-16 hrs. Streak 1 mL of each liquid culture in 200 μL aliquots onto LB/AMP plates and incubate at 37° C. overnight. Pick clones (e.g. 4) from LB/AMP plates and inoculate 5 mL LB/AMP broth in separate properly labeled 15 mL conical Falcon tubes. Loosely cover the tubes and place slanted in 37° C. shaker incubator for 12-16 hr. Extract DNA plasmid and detect NR1.1 of 2nd generation transformation using the protocols: DNA Extraction: Boiling Miniprep and NR1.1 Detection via PCR and Electrophoresis. FIG. 6 illustrates an electrophoresis gel showing NR1.1 bands of 1st and 2nd generation JM109 parentals exposed to DALM-coated nanoparticles (Fe).

FIG. 6 illustrates an electrophoresis gel illustrating JM109 parental, JM109pIC, 1st generation of DALM-coated Fe nanoparticle exposure and 2nd generation DALM-coated Fe nanoparticle exposure screened for the presence of NR1.1 (AMP resistant, nitrate reductase gene) as shown by asterisk (*). Primers Inner 1 Forward and Reverse and Inner 2 Forward and Reverse were also used to determine presence of NR1.1 within the gene.

Figure 7:
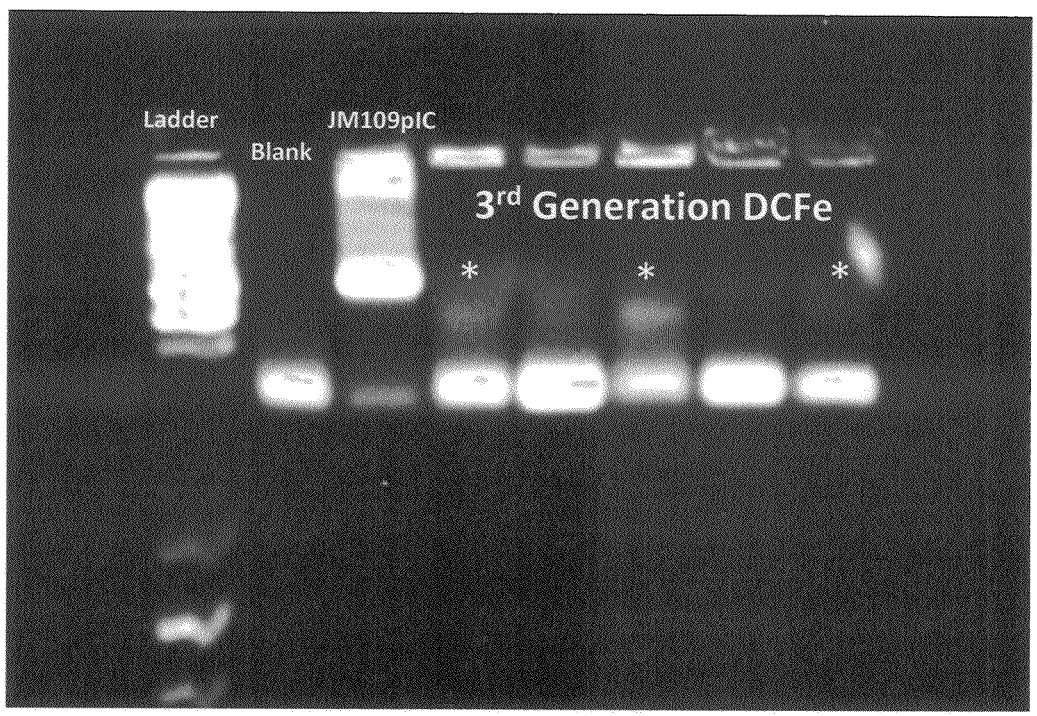
FIG. 7 represents an exemplary electrophoresis gel processing illustrating presence of a predetermined insert (as shown by asterisk (*)) after several transformations of a parent cell line in the presence of organic semiconductor associated nanoparticles, standards were included in the gel.

To obtain 3rd generation transformation, use clones of successful 2nd generation transformation and follow the protocols: Synthesis of 1st Generation Transformation DALM and JM109 parental strain exposed to DCFe of 1st Generation Transformation using DALM synthesized from 2nd generation clones. FIG. 7 represents an electrophoresis gel showing the presence of NR1.1 bands (*) in 3rd generation transformation of JM109 parent cells via DALM-coated Fe nanoparticles.

RPMI 1640 Medium

Using aseptic technique, under biological hood, 55 mL of RPMI 1640 Medium (Invitrogen, 0030078DJ) was extracted and pipetted into a properly labeled 50 mL conical Falcon tube and stored at 4° C.

MH-S Cell Line Propagation

MH-S cells (ATCC, CRL-2019), epithelial human lung macrophage, were grown in 150 cm3 tissue culture flasks (Fisher, 10-126-34) cultured in sterile-filtered RPMI 1640 Medium (Invitrogen, 003-0078DJ) supplemented with 3.5 μL/L of 2-mercaptoethanol (Sigma, M7522). Cells were kept in 37° C. incubator with 5% carbon dioxide atmosphere and subcultured to a 1:6 ratio when 85-90% confluent. Medium was refreshed every 2 to 3 days.

MH-S Subculturing

Remove medium from tissue culture flask, properly discard and replace with 4 mL of Trypsin-EDTA (Invitrogen, 25200-072) to disperse cells. Place flask in 37° C. incubator with 5% CO2 atmosphere for 5 min. Observe cells under an inverted microscope to ensure cell layer is dispersed. Add 10 mL of RPMI 1640 medium to inhibit Trypsin-EDTA and aspirate cells by gently pipetting. Transfer cell suspension into a 50 mL conical tube and centrifuge (Beckman Coulter, Allegra 6R) at 15° C., 2500 rpm for 5 min. Decant supernatant properly and resuspend cells in 12 mL of fresh RPMI 1640, gently aspirating cells. Place 2 mL into each of the 6 properly labeled tissue culture flasks containing 4 mL of medium and place flasks in 37° C. incubator with 5% $CO_2$ atmosphere.

MH-S Preservation/Freezing

Remove medium from tissue culture flask, properly discard and replace with 4 mL of Trypsin-EDTA (Invitrogen, 25200-072) to disperse cells. Place flask in 37° C. incubator with 5% CO2 atmosphere for 5 min. Observe cells under an inverted microscope to ensure cell layer is dispersed. Add 10 mL of RPMI 1640 medium to inhibit Trypsin-EDTA and aspirate cells by gently pipetting. Transfer cell suspension to 50 mL conical Falcon tube and centrifuge at 15° C., 2500 rpm for 5 min. Discard supernatant and resuspend cells in fresh RPMI 1640 medium (950 μL per 150 cm3 tissue flask). Pipet 50 μL of DMSO (Sigma, C6295) into each properly labeled cryongenic vial (Nalgene, 5005-0015) for each tissue culture flask and pipet 950 μL cell suspension into vial. Store vial in liquid nitrogen vapor phase after placing cell stock in a −80° C. freezer overnight.

MH-S Harvesting and Cell Concentration

Following the protocol of MH-S Subculturing, after adding fresh medium in step 6, collect the mixture from all respective flasks in a 50 mL conical tube and centrifuge at 15° C., 3000 rpm for 5 min. Discard supernatant and pipet 1 mL of medium to cells to determine cell concentration. Pipet 900 μL of medium and 100 μL of the 1 mL cell/medium mixture, previously mentioned, into a 15 mL conical tube and pipet 10 μL of that into a hemocytometer (Fisher, 0267110). Each grid of the hemocytometer represents a total volume of 0.1 mm3 or 10-4 cm3. Since 1 cm3 is equivalent to approximately 1 mL, the total number of cells per mL was determined using the following calculations: Cells/mL=average cell count per grid×dilution factor×104. This value is used to determine starting concentrations for confluency testing and cytotoxicity assays.

Confluency Testing

Using the value of cell concentration, previously mentioned above, starting concentrations of 1.04, 3.04, 5.04, and 7.04 cells/mL were placed into six designated wells of 24 well Falcon culture plates (Fisher 353047) data not shown. Plates were incubated at 37° C. with an air atmosphere of 5% $CO_2$ and evaluated for confluency at 24, 48 and 72 hours time intervals. After incubation periods, each well was observed for confluency percentage on an inverted microscope. The average percentage of respective concentrations for each time point was used in determining starting concentrations for the cytotoxicity assays which followed.

MH-S Confluency 72 hrs–4.5×10$^4$; 48 hrs–7.5×10$^4$; 24 hrs–1.5×10$^5$

XTT Cell Proliferation Assay

For each 24-well tissue culture plate, combine a 56 μL aliquot of the electron coupling reagent with a 2.8 mL aliquot of the XTT labeling reagent and vortex well. Pipet 100 μL into all wells and place back in 37° C. incubator with a 5% carbon dioxide atmosphere for 30 min. After the 30 min time interval, the plate was read at 490 nm (Bio-TEK, Synergy HT).

MH-S Exposure to DALM Cocktail

Harvest MH-S cells using phenol-free medium onto 24-well tissue culture plates with the respective cell concentration/per well with the exception of an empty "blank" well data not shown.

MH-S Exposure to Various Nanoparticles

A 10 μg/μL stock of the following nanoparticles was tested: Fe, Ag, FeAgC and FeC. In respective 15 mL Falcon tubes containing 5 mL of phenol-free RPMI 1640 medium, 10 μL of each stock is mixed. As mentioned earlier in MH-S Exposure to DALM Cocktail, expose the confluent MH-S cells to 1 mL the respective nanoparticle-medium mix, data not shown.

MH-S Exposure to DALM Coated Nanoparticles. Inverted microscopic images are represented of MH-S cells "taking up" the DALM-coated Fe nanopaticles at 40×, FIGS. 8C and 8D, and 100X, FIGS. 8A and 8B. Post exposure, conduct a DNA extraction of cells in the tissue culture flasks using the Qiagen Prep mentioned earlier and HeLa NR1 cells (ATCC, CRL-13011) as a positive control. FIGS. 9A and 9B represent an electrophoresis gel of these exemplary methods. FIG. 9A illustrates an electrophoresis gel of HeLa NR1 (positive control) and MH-S macrophages exposed to DALM-coated Fe nanoparticles and FIG. 9B represents the same gel as (A) only brighter to show bands clearer.

Pretreatment of MH-S with DALM Prior to Ampicillin Exposure

Figure 10:
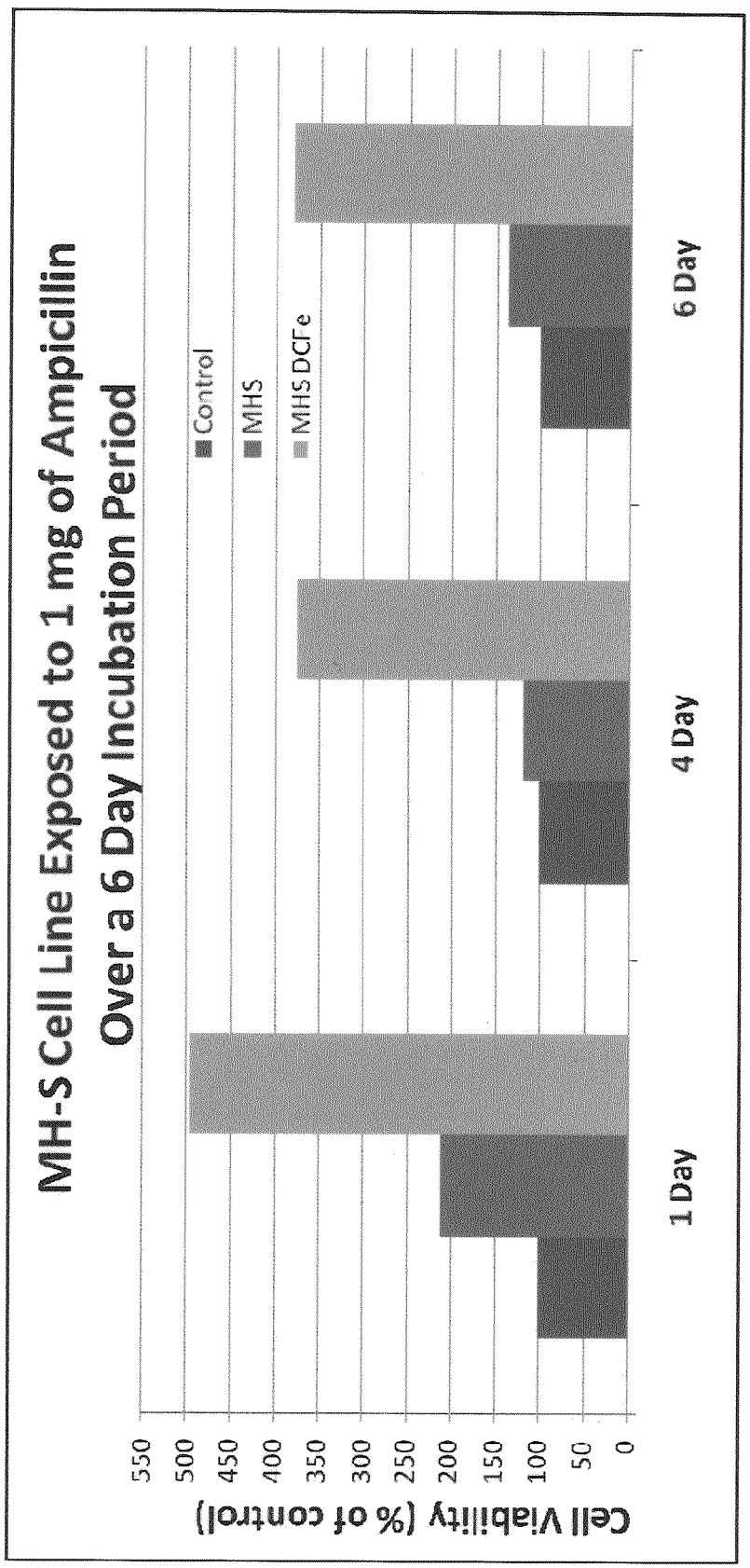
FIG. 10 represents an exemplary graph depicting a comparison of cells exposed to control compositions, control compositions plus predetermined selective agent compositions and control compositions plus predetermined selective agent compositions after a 24 hour pretreatment with organic semiconductor-coated nanoparticles of some embodiments of the present invention.

FIG. 10 illustrates an exemplary graph of a comparison of MH-S cells exposed to phenol-free medium (Control), phenol-free medium containing 5 mg/mL concentration of ampicillin (MH-S) and phenol-free medium containing 5 mg/mL concentration to ampicillin after a 24 hour pretreatment with DALM-coated nanoparticles. Here, the control is the same as MHS (phenol-free medium).

Random Aptamer Generation

In one example, a PCR chain termination step involved addition of 6.6 μg of random (N) 60 mer as a self-priming (due to partial hybridization) PCR template with 8 μg of each deoxy/dideoxynucleotide (e.g. d/ddA, d/ddC, d/ddG, d/ddT) and 20 μl (80 units) of Taq polymerase per tube. The tubes were PCR amplified using the following temperature profile: 96° C. for 5 min, followed by 40 cycles of 96° C. for 1 min, 25° C. for 1 min, and 72° C. for 1 min. PCR extension was completed at 72.degree. C. for 7 min and tubes were stored at 4 to 6° C. until electrophoresed. The collection of aptamers present as overlapping random (N) 60 mers or as ligated and truncated aptamers constituted a library of aptamers.

For both types of DNA arrays, 3.3 μg (typically 5 to 10 μl) of library DNA was diluted with 2×. loading buffer and loaded into each well of precast 10% or 4-20% gradient mini TBE polyacrylamide gels and electrophoresed in cold 1.times. TBE for 1 h at 100 V per gel. If DNA was to be visualized in the gel, gels were stained with 0.5 μg/ml ethidium bromide in TBE for 10 min, followed by rinsing in deionized water for 30 min and photography on a 300 nm ultraviolet transilluminator using Polaroid type 667 film.

Arrays of aptamers can be generated from library DNA separated by electrophoresis (size and charge). Analyte binding and nucleic acid hybridization to the aptamer arrays can be assayed as follows: Gels were cut into strips containing the one-dimensional DNA arrays of either type and were added to 10 ml of BB. Gel strips were allowed to equilibrate in their respective buffers for 10 min at room temperature (RT) with gentle shaking and were then scanned as described below prior to addition of analytes. All DNA analytes were added at a final concentration of 5 µg/ml and all protein analytes were added at a final concentration of 10 µg/ml in BB for 1 hr at RT with gentle shaking. Gels were gently rinsed twice in 10 ml of BB, carefully repositioned and rescanned on a luminescence spectrometer.

In one example, a Perkin-Elmer (Beaconsfield, Buckinghamshire, UK) model LS 50B luminescence spectrometer equipped with a plate reader was used in the thin layer chromatography (TLC) plate mode to scan DCE arrays in gel slices before and after addition of various analytes. After minor swelling or shrinkage in each of the reaction buffers, gel strips were generally 95 to 96 mm in length, with the DNA array being contained in the lower most 65 mm of each gel strip. Gel strips were scanned with an excitation of 260 nm (10 nm slits), emission of 420 nm (10 nm slits) and 1 mm resolution (i.e., scanned in 1 mm increments). ready for next aptamer selection. The aptamer/bio-agent/magnetic bead complex can be washed thoroughly with water. The aptamer of aptamer/bio-agent/magnetic bead complex can then be amplified by PCR or other suitable procedure. The amplified aptamers are cloned and then the aptamer can be sequenced.

Figure 11:
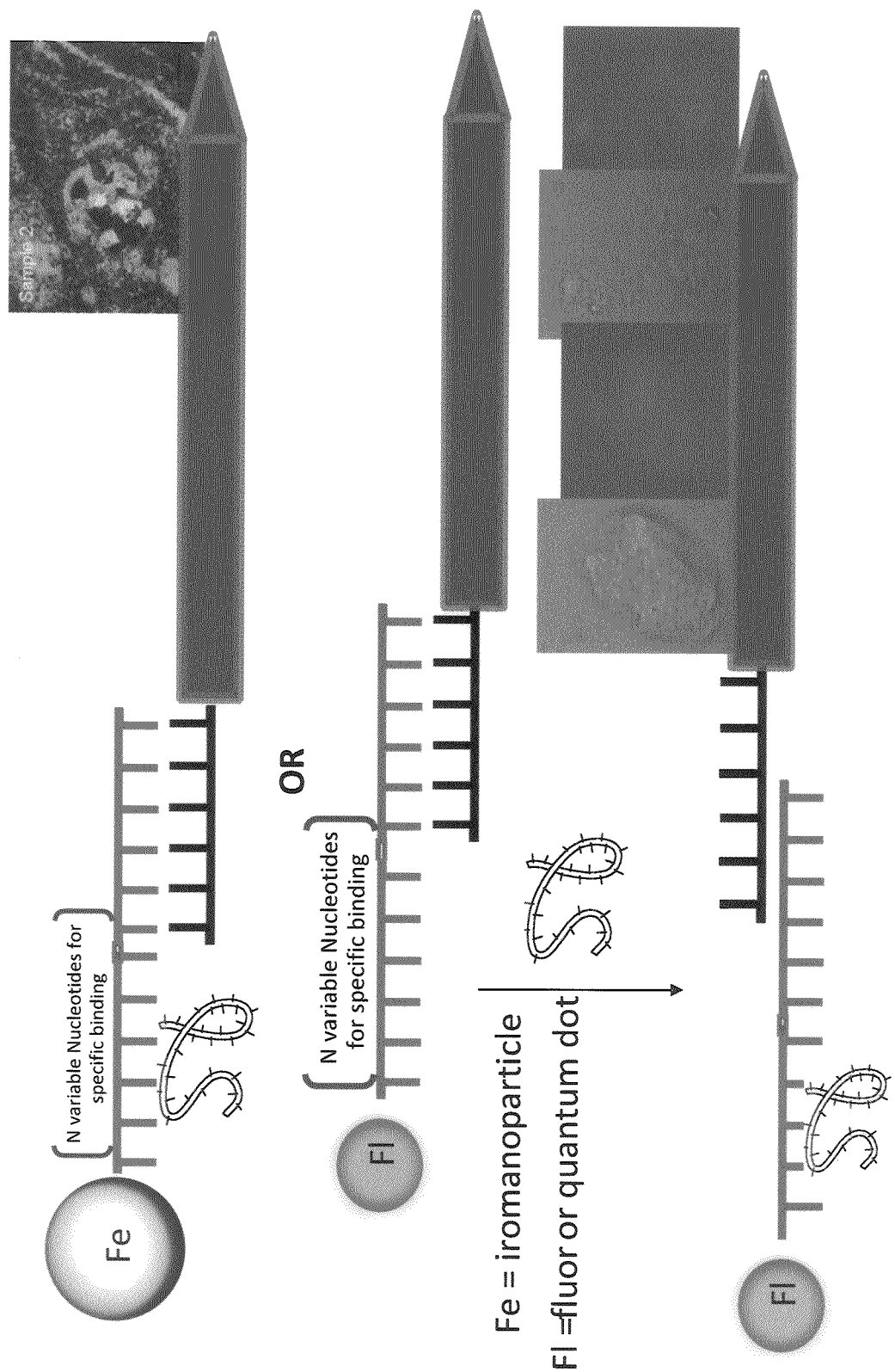
FIG. 11 represents the fluorescence of fluorophore (or Q-Dots) quenched by SWCNT (single-walled carbon nanotube).

FIG. 11 represents the fluorescence of fluorophore (or Q-Dots) quenched by SWCNT (single-walled carbon nanotube) before a SWCNT/primer/(DNA)aptamer/fluorophore complex penetrates a cell. After the complex penetrates a cell membrane, the DNA (aptamer) can be denatured from a primer, and the fluorescence detectability returns. The microscope images illustrates the fluorescence (e.g. Nikon ECLIPSE E800). As used herein "fluor" can be a "fluorophore."

Dequenching of Double-Stranded DNA Capture Element (Aptamer) Fluor on Carbon Nanotube by Addition of Target (known to bind to aptamer FIG. 12 represents fluorescent change after bacterial spores (e.g. Bt and Ba) are introduced into an quenching system (e.g. Bt aptamer). In this example, a SWCNT was used as quencher. The microscope images demonstrate fluorescence after spores (e.g. Bt) were introduced into the quenching system. The primary strand of Bt aptamer is connected to carbon nanotube. The fluorophore (Hylite 488) is connected to complementary strand. The two strands of aptamer are annealed together. Fluorescent Change of Bt DCE after Bt and Ba spores introduced into the system (Single-wall carbon nanotube as a quencher, fluorophore wavelength is 529 nm). The fluorescent intensity rises dramatically upon binding of the target agent.

Figure 13:
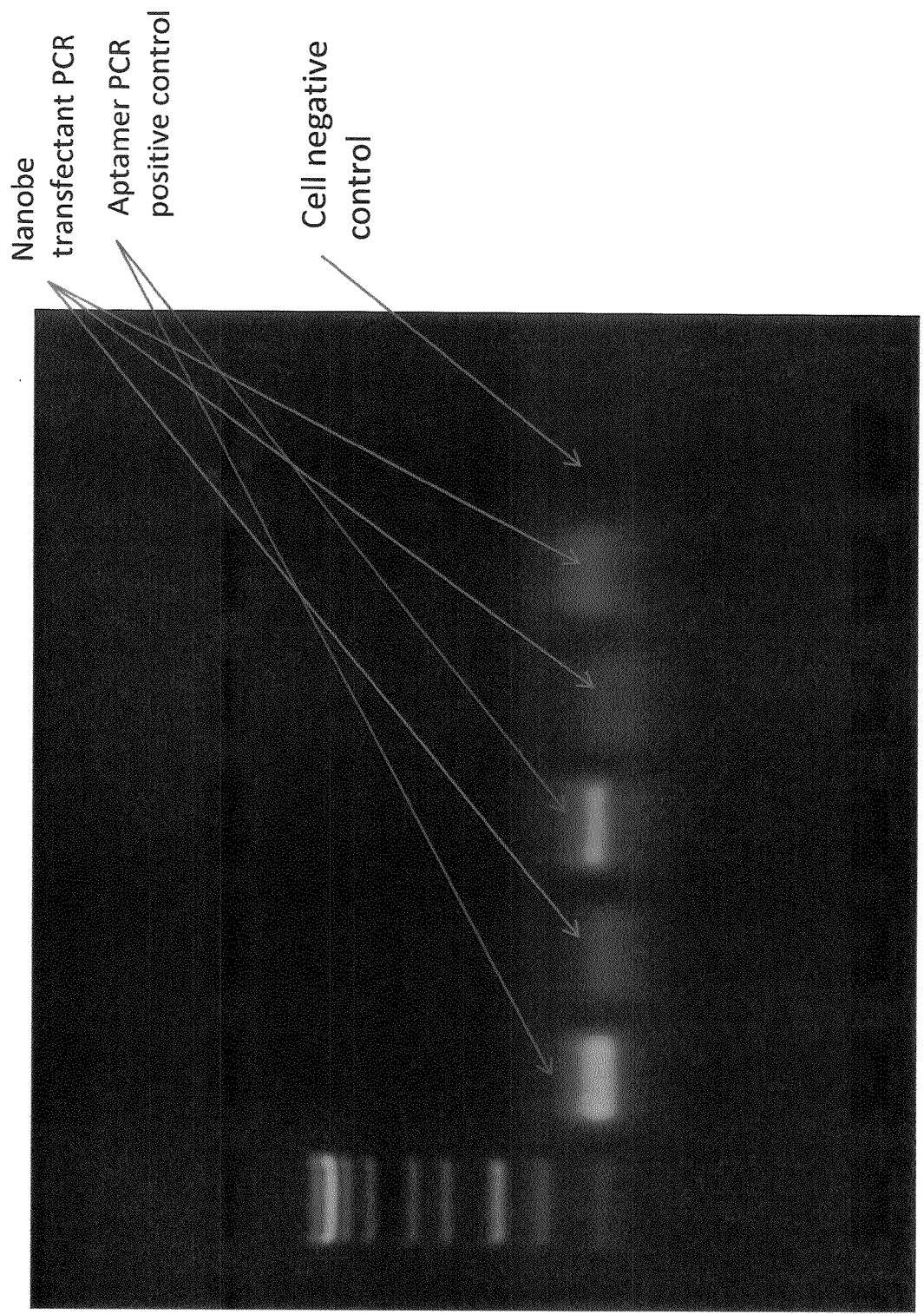
FIG. 13 represents a gel separation of various constructs.

Aptamer Transfection of Mouse Macrophages (MH-S) using Carbon Nanotubes with Double-Stranded Artificial DNA Hybridized to Primer Complementary Strand. FIG. 13 represents a gel separation of various constructs. Band from left to right: 1. DNA ladder; 2 and 4. Bt aptamer as control; 3, 5, and 6. sample comes from: (a) interaction of SWCNT/primer/ss-aptamer/fl with Macrophages, (b). the SWCNT/primer/aptamer-fl-Cell of Microphages was treated with DNase; (c). The DNased of SWCNT/primer/aptamer/fl-Cell of Microphages was treated with RIPA buffer; 7. Macrophage cell as negative control 4 comes from 2 (e.g. second round PCR), 5 comes from 3 (e.g second round PCR), and 6 comes from 5 (e.g third round PCR).

Figure 14:
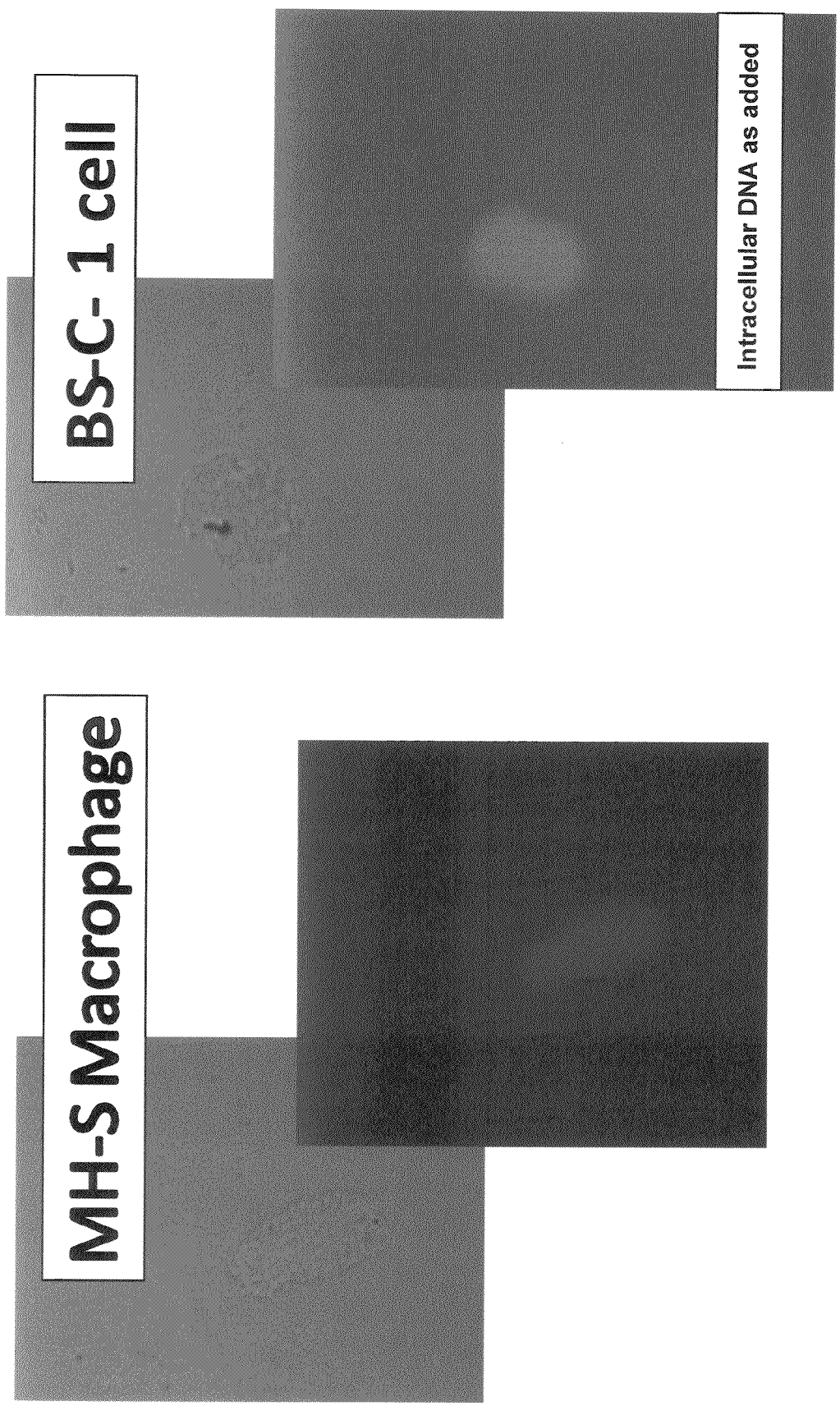
FIG. 14 represents microscopic images illustrating fluorescence of various constructs.

Dequenching of Fluorochrome/Carbon Nanotube Double-Stranded DNA Aptamer Conjugates in Eukaryotic Cells. FIG. 14 represents microscopic images illustrating fluorescence after (1). Interacting of SWCNT/primer/aptamer/FL with Microphage cell (2). Interacting of SWCNT/ds-aptamer/FL with BS-C-1 cell and indicate that SWCNT/primer/aptamer/FL complex and SWCNT/ds-aptamer/FL complex penetrate the cell membrane and the ds-DNAs were denatured.

Figure 15:
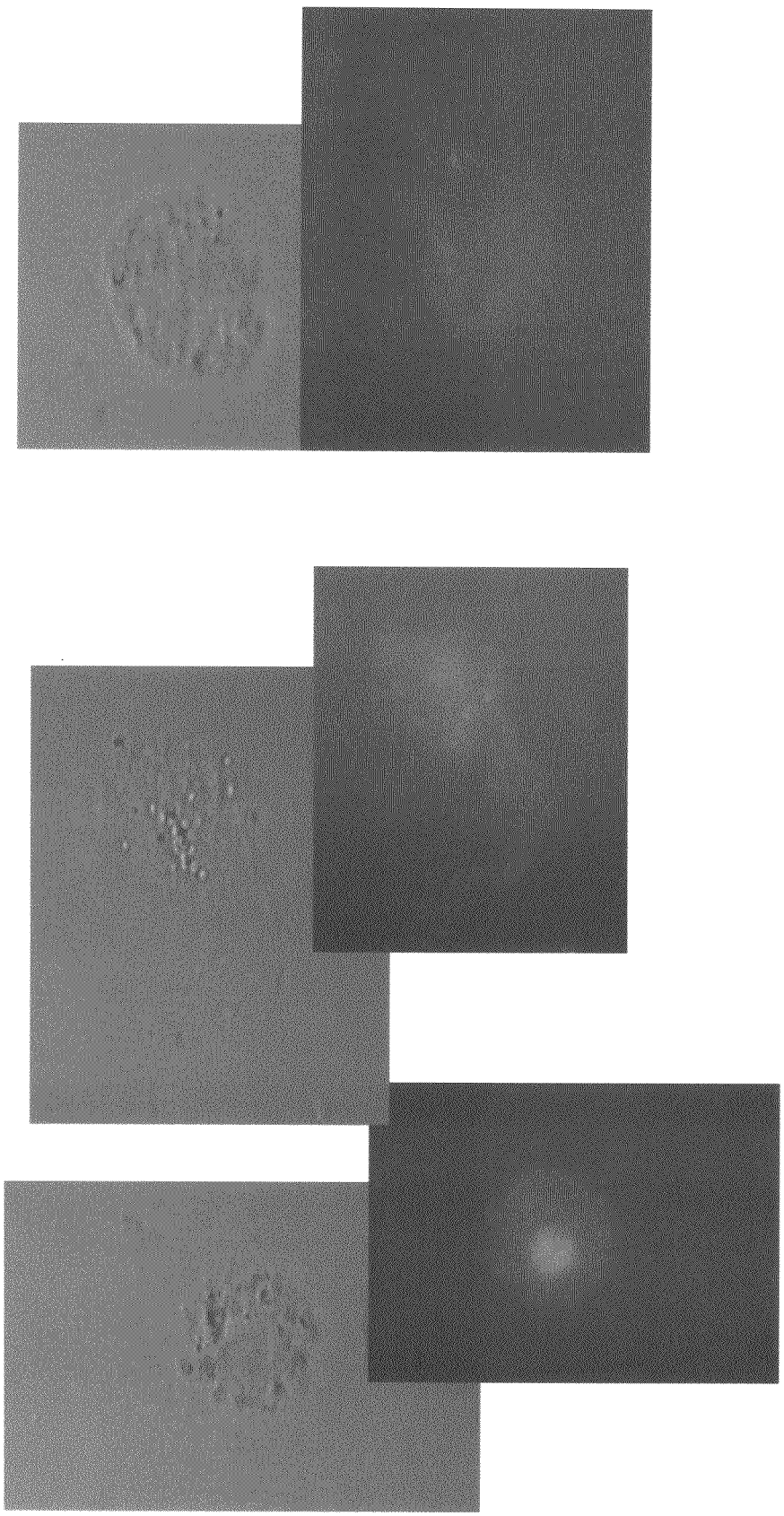
FIG. 15 represents microscopic images illustrating fluorescence after interactions of various constructs.

HeLa-P6 cell line with SWCNT/dsDNA-aptamer/Q-dots FIG. 15 represents microscopic images illustrating fluorescence after interaction of HeLa-P6 cell line with SWCNT/ds-aptamer/Q-dots complex and indicate that the ds-aptamer was denatured after the complex penetrates the cell membrane.

Interaction of BS-C-1 Cell Lines with SWCNT/ds-Aptamer/Fluorophore

Figure 16:
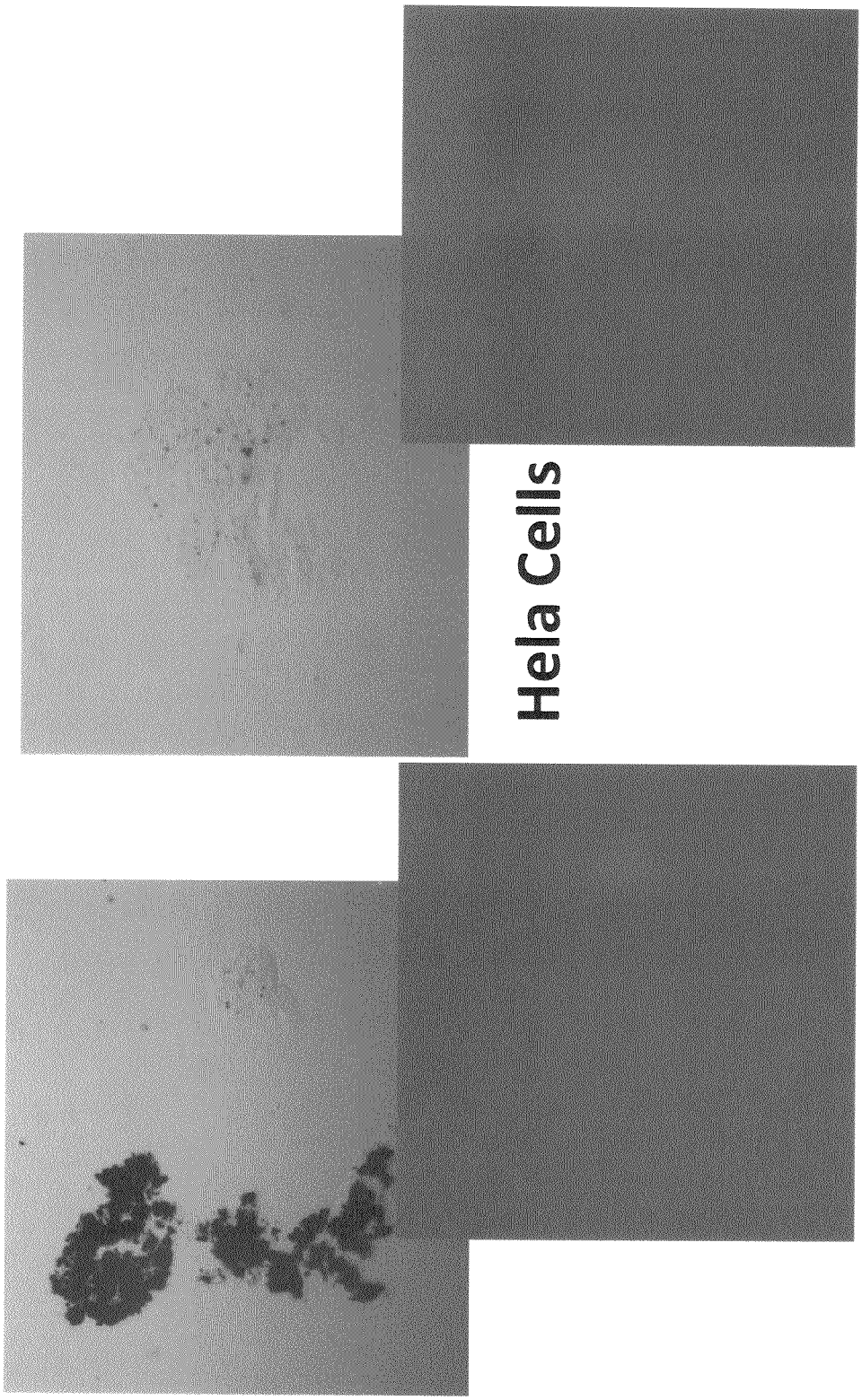
FIG. 16 represents microscope images (left side) illustrating fluorescence after interaction of a cell line with a construct.

Carbon Nanotubes with DNA, Fluor, in Cells FIG. 16 represents (1) microscopic images (left side) illustrating fluorescence after interaction of BS-C-1 cell line with SWCNT/ds-aptamer/FL complex and indicate that the ds-aptamer was denatured (right section) after the complex penetrates the cell membrane. Undenatured (left section) SWCNT/ds-aptamer/FL complexes did not demonstrate fluorescence which is quenched by SWCNT (2). Microscope images (right side) illustrate fluorescence after interaction of HeLa-P6 cell line with SWCNT/ds-aptamer/FL complex and indicate that the ds-aptamer was denatured after the complex penetrates the cell membrane. Interactions of BS-C-1 and hela-P6 cell lines with SWCNT/ds-aptamer/fluorophore. (1). 10 µL of SWCNT/ds-aptamer/fluorophore are added in 150 µL of BS-C-1 cell lines (in media). The mixture is shaken at 37° C. for 2 days (Incubator). 5 µL of the mixture is saved for PCR (see the image of electrophoresis of the sample) and 1 µL is used for microscope. The microscope image of BS-C-1 cell/SWCNT/ds-aptamer/fluorophore complex is at 530 nm wavelength (top). The microscope image of BS-C-1 cell/SWCNT/ds-aptamer/fluorophore complex at range of visible wavelength (bottom).

Most of Fluorescence is Quenched by SWCNT

The BS-C-1 cell/SWCNT/ds-aptamer/fluorophore complex is spun down and washed with sterile H2O three times. The washed BS-C-1 cell/SWCNT/ds-aptamer/fluorophore complex is re-suspended in 200 µL of sterile H2O and 20 µL of DNase (212 unit/µL, Invitrogen) are added. The mixture is shaken at R.T for 2 hours and the DNased BS-C-1 cell/SWCNT/ds-aptamer/fluorophore complex is spun down and washed three times with $H_2O$. The washed DNased BS-C-1 cell/SWCNT/ds-aptamer/fluorophore complex is re-suspended in 200 µl of H2O and 5 µl are saved for PCR (see the image of electrophoresis of the sample).

(3). The DNased BS-C-1 cell/SWCNT/ds-aptamer/fluorophore complex (from (2)) is spun down and 100 µL of RIPA buffer are added. The mixture is shaken at 37° C. over weekend. 5 µl of the mixture are saved for PCR (see the image of electrophoresis of the sample).

Interaction of Hela-P6 Cell Lines with SWCNT/ds-Aptamer/Fluorophore (1). 10 µl of SWCNT/ds-aptamer/fluorophore are added in 150 µl of Hela-P6 cell lines (in media, from Melanie). The mixture is shaken at 37° C. for 2 days (Incubator). 5 µL of the mixture is saved for PCR (see the image of electrophoresis of the sample) and 1 µL is used for microscope. The microscope image of HeLa-P6 cell/SWCNT/ds-aptamer/fluorophore complex is represented at range of visible wavelength (top). The microscope image of HeLa-P6 cell/SWCNT/ds-aptamer/fluorophore complex is represented at 530 nm wavelength (bottom).

(2). The HeLa-P6 cell/SWCNT/ds-aptamer/fluorophore complex is spun down and washed with sterile $H_2O$ three times. The washed HeLa cell/SWCNT/ds-aptamer/fluorophore complex is re-suspended in 200 µl of sterile $H_2O$ and 20 µL of DNase (212 unit/µl, Invitrogen) are added. The mixture is shaken at R.T for 2 hours and the DNased HeLa-P6 cell/SWCNT/ds-aptamer/fluorophore complex is spun down and washed three times with H$_2$O. The washed DNased HeLa-P6 cell/SWCNT/ds-aptamer/fluorophore complex is re-suspended in 200 µl of H$_2$O and 5 µl are saved for PCR (see the image of electrophoresis of the sample). (3). The DNased HeLa-P6 cell/SWCNT/ds-aptamer/fluorophore complex (from (2)) is spun down and 100 µL of RIPA buffer are added. The mixture is shaken at 37° C. for a couple of days. 5 uL of the mixture are saved for PCR (see the image of electrophoresis of the sample). An electrophoresis image of HeLa-P6 cell/SWCNT/ds-aptamer/fluorophore and BS-C-1 cell/SWCNT/ds-aptamer/fluorophore complexes is demonstrated (data not shown). For BS-C-1 cell/SWCNT/ds-aptamer/fluorophore complex, the outside Bt aptamers of the cell are destroyed by DNase. The gel illustrated a band after lysis of BS-C-1 cell/SWCNT/ds-aptamer/fluorophore complex. This band indicates that the SWCNT connected ds-Bt aptamer with fluorophore penetrate the BS-C-1 cell. For HeLa-P6 cell/SWCNT/ds-aptamer/fluorophore complex, the sample of DNased of HeLa-P6 cell/SWCNT/ds-aptamer/fluorophore [from (2)] illustrates the band and the lysed sample shows no band. The interaction of SWCNT/ds-aptamer/fluorophore complex with HeLa-P6 was repeated and the electrophoresis illustrated the same result.

Figure 17:
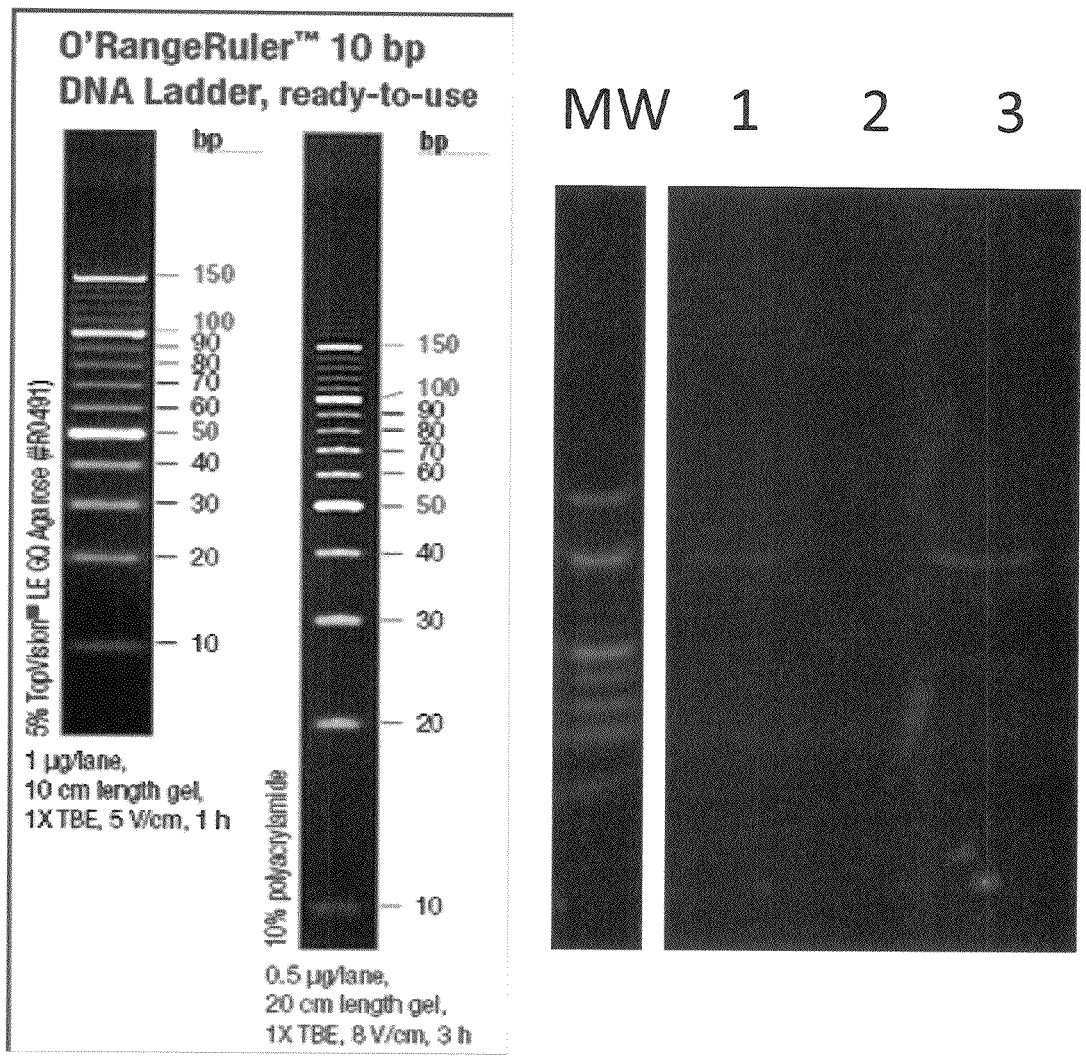
FIG. 17 represents an electrophoretic gel of constructs under various conditions of digestion with DNase.

PCR Results on Carbon Nanotube/DNA/Fluor Nanobes in Cells FIG. 17 represents that electrophoresis does not show band (band 2) that indicates that the outside aptamers of SWCNT/ds-aptamer/FL-BS-C-1 cell complex are degraded by DNase. Electrophoresis illustrates band (band 3) that indicates that the aptamers of inside cell are released after the cell membrane of BS-C-1 is destroyed by buffer (e.g. RIPA). 1. BS-C-1 Cell/SWCNT-ds-aptamer-fluorophore complex 2. DNased of BS-C-1 Cell/SWCNT-ds-aptamer-fluorophore complex 3. Lysed BS-C-1 Cell/SWCNT-ds-aptamer-fluorophore complex.

Figure 18:
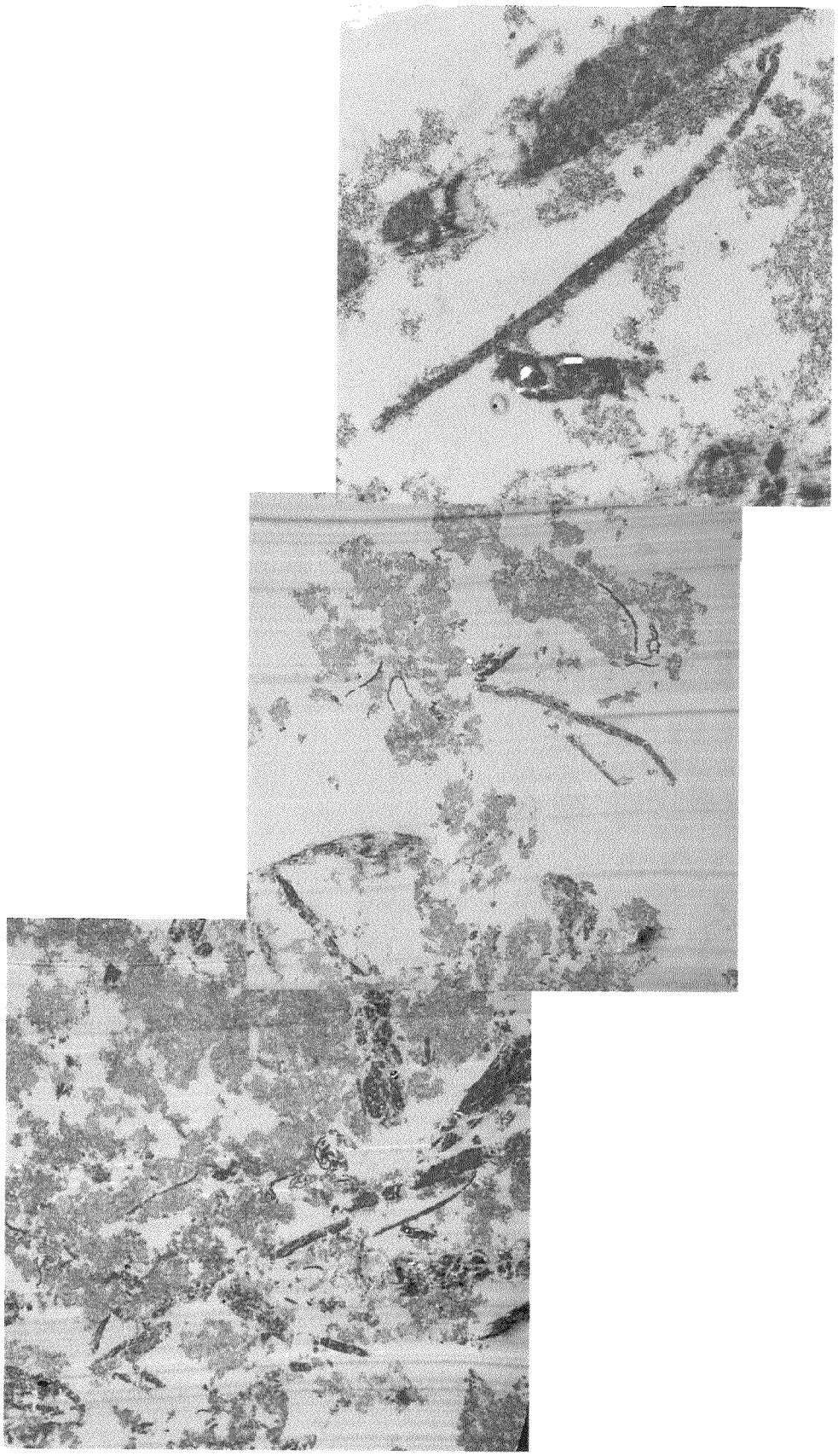
FIG. 18 represents TEM images indicate of various complexes that can penetrate the cell membrane.

Preparation of HeLa-P6 cell/SWCNT/ds-Aptamer/Q-Dots and FeO (Nano Particles) Complexes for TEM 10 µl of SWCNT/ds-aptamer/Q-dots and 10 µl of SWCNT/ds-aptamer/FeO (nanoparticles, 15 nm) are added in 100 µL of HeLa-P6 cell line respectively. The mixtures are shaken at 37° C. for 2 days (Incubator) and saved for TEM. FIG. 18: represents TEM images indicate of SWCNT/aptamer/DNA/iron nanoparticle complexes that can penetrate the cell membrane.

Figure 19:
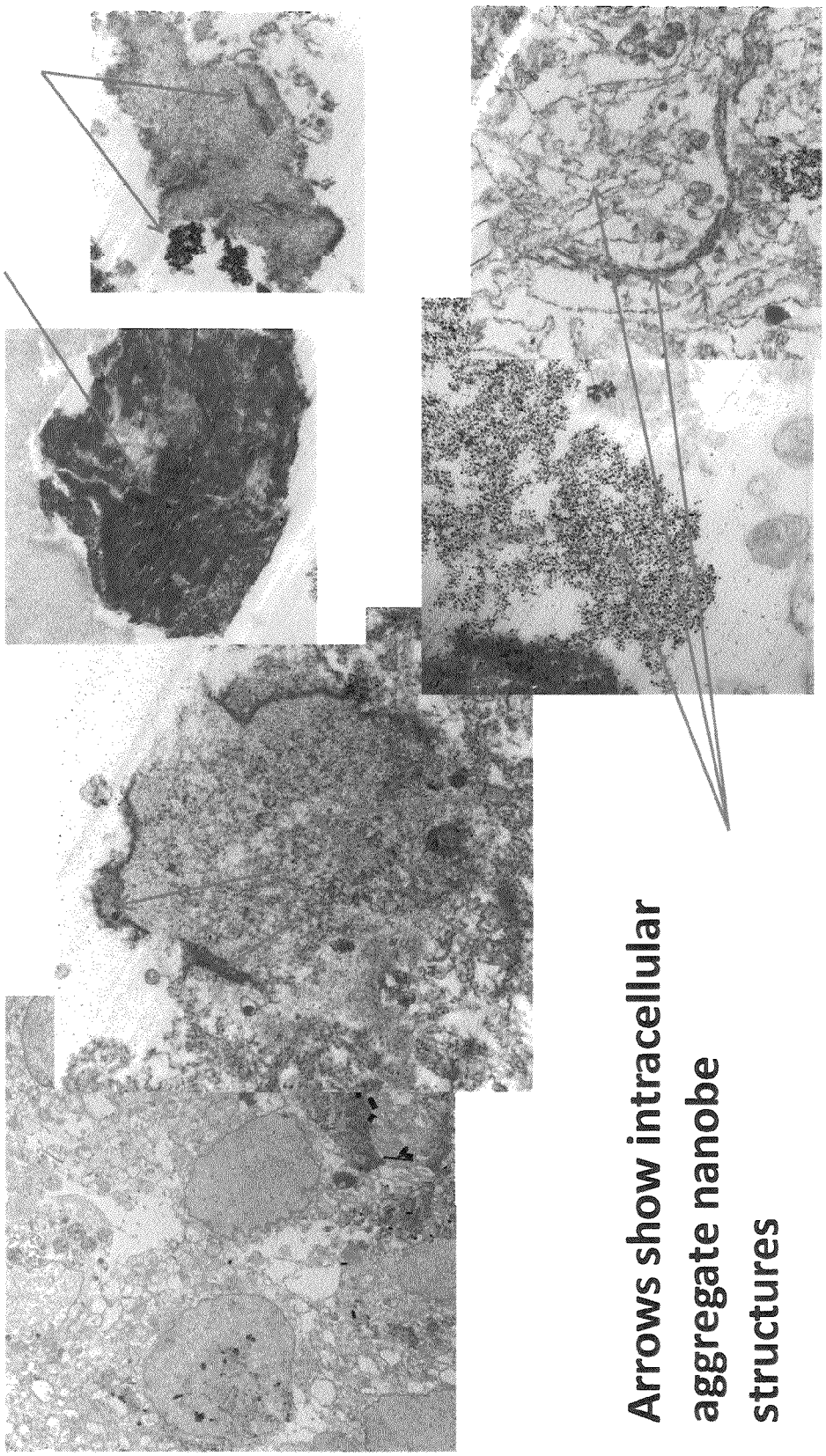
FIG. 19 represents TEM images indicate of various complexes that can penetrate the cell membrane with arrows indicating intracellular aggregate nanobe structures.

Preparation of BS-C-1 Cell/SWCNT/ds-Aptamer/FeO (Nano Particles) Complexes for TEM 10 µl of SWCNT/ds-aptamer/FeO (nanoparticles, 15 nm) are added in 100 µL of BS-C-1 cell. The mixtures are shaken at 37° C. for 2 days (Incubator) and saved for TEM. FIG. 19 represents TEM images indicate of SWCNT/aptamer/DNA/iron nanoparticle complexes that can penetrate the cell membrane with arrows indicating intracellular aggregate nanobe structures.

Materials, Protocols and Methods

Conjugation of single wall carbon nano tube (SWCBT) with phosphatidyl serine; with DNA primer; with DNA primer and complementary fluorophore labeled aptamer. The SWCNT with a carboxyl functional group was purchased (e.g. Sun Innovation Inc.) and phosphatidyl serine was obtained (e.g. Signa-Aldrich; 1,2-Diacyl-sn-glycero-3-phospho-L-serine; Product Name: P7769)

Preparation of SWCNT-Phosphatidyl Serine (1). Covalent bonding between SWCNT and phosphatidyl serine: about 1 mg phosphatidyl serine is added to small amount of SWCNT in 0.01M MOPs buffer and 15 mg EDC and 5 mg imidazole are added. The reaction mixture was stirred overnight. The product, SWCNT-phosphatidyl serine, is separated and washed with water and re-suspended in 1 ml PBS buffer.

Non-covalent bonding between SWCNT and phosphatidyl serine: about 1 mg phosphatidyl serine is added to small amount of SWCNT in 0.01M MOPs buffer. The reaction mixture was stirred over weekend. The SWCNT-phosphatidyl serine (non-covalent bonding) is separated and washed, then re-suspended in 1 ml PBS buffer.

Preparations of SWCNT Primer, SWCNT-Primer/Aptamer and SWCNT-Primer/Aptamer-Q-Dots (1). About 0.5 µl L of primer (Forword or Reverse) with —NH2 functional group (F: 6.25×10^11 DNA/µL or R: 6.88×11^11 DNA/µL) are added to a small amount of SWCNT in 0.1M MOPS buffer respectively. Then 15 mg EDC and 5 mg imidazole are added. The mixture is stirred overnight. The SWCNT-primer (F or R) are separated and washed, then re-suspended in TE buffer. (2). 0.5 µL of Bt aptamer (primary or complementary strand) are added to SWCNT-Primer (F or R) respectively, (of note, the 3' side primer of aptamer should be complementary to the primer bound to the SWCNT and 5' side of the aptamer is —PO4 functional group). The mixture is stirred overnight, then separated and washed. The SWCNT-primer/aptamer is re-suspended in TE buffer.

Preparations of SWCNT/ss-Aptamer, SWCNT/ds-Aptamer and SWCNT/ds-Aptamer/Q-Dots (1). 10 µl of Bt aptamer (complementary, —NH2 functional group, 1.4×10^13 DNA/µL) are added to a small amount of SWCNT in 0.1M MOPs buffer. Then 60 mg EDC and 20 mg imidazole are added. The mixture is stirred overnight. The SWCNT-ss-aptamer is separated and washed, then re-suspended in 0.1M MOPs buffer. (2). 15 µL of Bt aptamer (primary, —PO4 functional group, 1.3×10^13 DNA/µL) are added to the SWCNT/ss-aptamer in 0.1M MOPs buffer. The mixture is stirred at 60° C. for 6 hr and R.T. overnight. The SWCNT/ds-aptamer is separated and washed, then re-suspended in 0.1M MOPS buffer. (3). 200 µl of Q-dots are added to the SWCNT/ds-aptamer in 0.1M MOPS buffer. Then 60 mg EDC and 20 mg imidazole are added. The mixture is stirred overnight. The product, SWCNT/ds-aptamer/Q-dots, is separated and washed, and re-suspended in 2 ml PBS buffer.

After PCR of SWCNT-Primer/aptamer, the image of the gel illustrates a clear band with pure Bt aptamer as positive control. (3). 100 ul of Q-dots (—NH2 functional group) are added to the SWCNT-Primer/Aptamer in 0.1M MOPs buffer. Then 30 mg EDC and 10 mg imidazole are added. The mixture is stirred overnight. The SWCNT-Primer/Aptamer-Q-dots is separated and washed with water, then re-suspended in PBS buffer.

Preparations of SWCNT (nanotube, quenching agent)-ss-aptamer, SWCNT-ds-aptamer, and SWCNT-ds-aptamer-Fluorophore 10 µl of Bt aptamer (complementary, 5' side was —NH2 functional group, 1.4×10^13 DNA/µL) are added to a predetermined amount of SWCNT in 0.1M MOPs buffer. Then 60 mg EDC and 20 mg imidazole are added. The mixture was stirred overnight. The SWCNT-ss-aptamer was separated and washed, then re-suspended in 0.1M MOPs buffer. 15 µA of Bt aptamer (primary, 5' side was —PO4 functional group, 1.3×10^13 DNA/µL) are added to the SWCNT-ss-aptamer in 0.1M MOPs buffer. The mixture was stirred at 60 degree C. for 6 hr and R.T. overnight. The SWCNT-ds-aptamer is separated and washed, then re-suspended in 0.1M MOPs buffer. 15 µl of fluorophore (Hylyte Fluor. 488, 1×10^14 molecule/µL; Anaspec, Inc) are added to the SWCNT-ds-aptamer in 0.1M MOPs buffer. Then 60 mg EDC and 20 mg imidazole are added. The mixture was stirred overnight. The product, SWCNT-ds-aptamer-fluorophore, was separated and washed, and re-suspended in PBS buffer. (The fluorescence was quenched by SWCNT. The fluorescence comes back after interaction of SWCNT-ds-aptamer-fluorophore with Bt spores).

All of the COMPOSITIONS and/or METHODS and/or APPARATUS disclosed and claimed herein can be made and executed without undue experimentation in light of the present disclosure. While the compositions and methods have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of herein. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed:

1. A plasmid complex composition comprising:

one or more plasmids each having an unselected aptamer inserted into the one or more plasmids to make random aptamer-plasmid complexes, wherein the unselected aptamer is not yet selected to bind to a target; and an organic semiconductor associated with the one or more plasmids, wherein the random aptamer-plasmid complexes and the organic semiconductor form random aptamer-plasmid-organic semiconductor complexes.

2. The composition of claim 1, wherein the random aptamer-plasmid-organic semiconductor complexes are associated with nanoparticles or microbeads.

3. The composition of claim 2, wherein the nanoparticles immobilize the random aptamer-plasmid-organic semiconductor complexes.

4. The composition of claim 2, wherein the nanoparticles or microbeads are selected from the group consisting of paramagnetic nanoparticles, quantum dots, nanostructures, colloidal gold, colloidal silver, iron nanoparticles, platinum nanoparticles, microspheres, or nanospheres.

5. The composition of claim 1, wherein the organic semiconductor comprises DAT or DALM or other organic semiconductor.

6. The composition of claim 1, wherein the target comprises a protein, peptide, polysaccharide, lipid, or nucleic acid.

7. The composition of claim 1, wherein the random aptamer-plasmid-organic semiconductor complexes are further immobilized on a solid substrate.

8. The composition of claim 1, wherein the target comprises a virus, a yeast, a spore, a bacterium, a disorder-associated molecule, a disease-progression molecule, a disease marker or a combination thereof.

9. A plasmid-complex composition comprising:

one or more plasmids each having an unselected aptamer inserted into the one or more plasmids to make random aptamer-plasmid complexes, wherein the unselected aptamer is not yet selected to bind to a target; and an organic semiconductor, DALM, associated with the one or more plasmids, wherein the random aptamer-plasmid complexes and DALM form random aptamer-plasmid-DALM complexes.

10. The composition of claim 9, wherein the random aptamer-plasmid-DALM complexes are associated with nanoparticles.

11. The composition of claim 10, wherein the nanoparticles immobilize the random aptamer-plasmid-DALM complexes.

12. The composition of claim 10, wherein the nanoparticles comprise paramagnetic nanoparticles, iron nanoparticles, platinum nanoparticles or other paramagnetic nanoparticles.

13. The composition of claim 9, wherein the target is a protein or protein complex.

14. The composition of claim 9, wherein the random aptamer-plasmid-DALM complexes are further immobilized on a solid substrate.

15. The composition of claim 9, wherein the target is a bacterium.

* * * * *